United States Patent [19]

Möller et al.

[11] Patent Number: 4,785,830

[45] Date of Patent: Nov. 22, 1988

[54] METHOD AND APPARATUS FOR MONITORING AND EVALUATING THE DENSITY OF A TOBACCO STREAM

[75] Inventors: Henning Möller; Werner Hartmann, both of Hamburg, Fed. Rep. of Germany

[73] Assignee: Körber AG, Hamburg, Fed. Rep. of Germany

[21] Appl. No.: 572,563

[22] Filed: Jan. 18, 1984

[30] Foreign Application Priority Data

Jan. 22, 1983 [DE] Fed. Rep. of Germany ....... 3302058

[51] Int. Cl.$^4$ ................................................. A24C 5/14
[52] U.S. Cl. .................................. 131/84.1; 131/84.2; 131/84.3; 131/84.4; 131/281; 131/905; 131/906; 131/108
[58] Field of Search ..................... 131/84.1, 84.3, 84.2, 131/84.4, 905, 108, 906, 109.1, 281

[56] References Cited

U.S. PATENT DOCUMENTS

| | | | |
|---|---|---|---|
| 3,056,026 | 9/1962 | Bigelow | 131/84.1 |
| 4,175,570 | 11/1979 | Heitmann | 131/84.1 |
| 4,185,644 | 1/1988 | Heitmann et al. | 131/84.1 |
| 4,281,670 | 8/1981 | Heitmann et al. | 131/281 |
| 4,287,754 | 9/1981 | Heitmann et al. | 131/281 |

*Primary Examiner*—V. Millin
*Assistant Examiner*—J. Cheng
*Attorney, Agent, or Firm*—Peter K. Kontler

[57] ABSTRACT

A continuous stream of tobacco shreds is built at the underside of the lower reach of an air-permeable belt conveyor by conveying tobacco shreds in currents of air which impinge upon the lower reach of the conveyor at a variable angle and at a variable speed. The density of various layers of the stream at a plurality of points at different distances from the lower reach of the conveyor is monitored by a device which directs X-rays transversely across the stream and has a uni- or two-dimensional detector with one or more rows of diodes exposed to X-rays which have penetrated through the stream. The signals which are thereby generated by the diodes denote the monitored density at the plurality of points and are scanned, evaluated and processed to actuate one or more servomotors which vary one or more parameters that influence the orientation of shreds in the stream, the density and/or other characteristics of the stream. Such parameters can include the subatmospheric pressure at one side of the lower reach of the conveyor, the direction of flow, speed and/or quantity of air which transports the shreds to the conveyor, the rate of admission of tobacco shreds into the air current or currents, and/or the position of the trimming device which removes the surplus from the stream. The signals can be used to vary the parameters which influence the characteristics of the entire stream and/or to vary one or more parameters which influence the density and/or other characteristics of one or more layers of the stream.

50 Claims, 6 Drawing Sheets

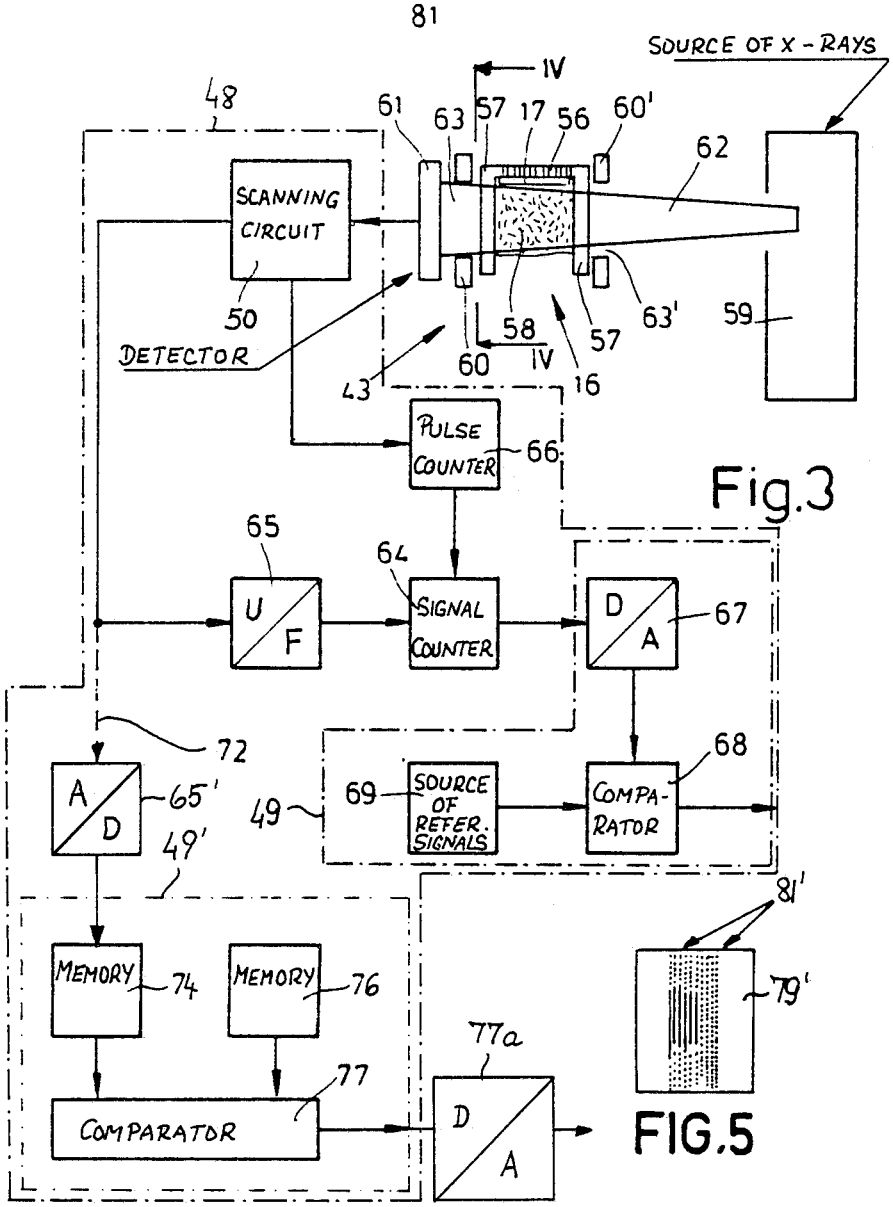

METHOD AND APPARATUS FOR MONITORING AND EVALUATING THE DENSITY OF A TOBACCO STREAM

BACKGROUND OF THE INVENTION

The present invention relates to a method of and to an apparatus for forming and processing a stream of fibrous material, particularly a stream of natural, reconstituted and/or substitute tobacco which can be converted into the rod-like filler of a cigarette rod or the like. More particularly, the invention relates to improvements in a method of and in an apparatus for forming a stream which is obtained by accumulating fibrous material into successive increments of the stream, conveying such increments along an elongated path, monitoring the density of successive increments of the stream, and influencing one or more parameters which determine the characteristics of the stream as a function of fluctuations of the monitored density. A thus treated stream can be used for conversion into a constituent of a rod that is ready for subdivision into filter rod sections, plain cigarettes, cigarillos and like rod-shaped articles which constitute or form part of smokers' products. For the sake of simplicity, the following description of the invention and of conventional methods and apparatus will deal with a method and apparatus for the making of a stream which is converted into the filler of a cigarette rod with the understanding, however, that such method and apparatus can be resorted to with equal advantage for the making of streams which are ready for conversion into or which constitute rod-like fillers for other types of smokers' products or constituents of smokers' products.

Timely ascertainment of various characteristics of a tobacco stream is highly desirable and advantageous because this renders it possible to immediately or practically immediately undertake the necessary corrective measures when the quality of the finished product or of an intermediate product deviates from an optimum quality. For example, it is desirable and advantageous to ascertain the density of the tobacco stream which is about to be converted into or which already constitutes the filler of a cigarette rod. Timely detection of the distribution of density in the longitudinal direction of the tobacco stream ensures that the cigarette making machine will not turn out excessive numbers of cigarettes with soft ends which are conducive to escape of tobacco shreds with attendant contamination of the pocket, purse, table top, floor and/or the interior of the pack. Thus, timely detection of various characteristics, particularly density, of a tobacco stream renders it possible to achieve a great reduction in the number of rejects, customer complaints, distributor complaints and switches to different makes of cigarettes.

The results of the measurements of density of a tobacco stream are used with advantage for regulation of the make-up (composition) of the stream for a large number of years. In accordance with a presently known proposal, the density of the tobacco stream is monitored by a detector which employs a source of beta rays and a transducer in the form of an ionization chamber serving to generate electric signals which are indicative of the density of successive unit lengths of the stream. A drawback of such mode of measuring the density of a tobacco stream is that the measurement is not sufficiently accurate and that the inertia of the detector is high, primarily due to the characteristics of the ionization chamber. Moreover, such detectors are merely capable of generating signals which are indicative of the average density of the monitored stream, i.e., the signals are actually integrals of the densities in various cross-sectional areas of the stream. In other words, the just discussed conventional measurement of density cannot furnish any information regarding the distribution of density in various sections of the stream, such as at the center, close to the periphery or midway between the periphery and the center of the stream.

U.S. Pat. No. 3,056,026 to Bigelow discloses a cigarette density gage which utilizes a source of X-rays in conjunction with a dual ion chamber. The ion chamber is designed to transmit electric signals which are indicative of the average density of the stream, i.e., of an integral of density across the entire cross-section of the monitored portion of the stream. The gage of Bigelow also fails to furnish any information which could be used to ascertain the distribution of density in selected portions of a tobacco stream, as considered at right angles to the longitudinal axis of the stream. On the other hand, timely detection of density variations in various strata of the tobacco stream, in addition to or in lieu of detection of eventual fluctuations of density as considered in the longitudinal direction of the stream, could assist the manufacturer in carrying out adjustments which would greatly enhance the quality of the ultimate product, which would bring about pronounced savings in tobacco, which would reduce the number of rejects and/or which would reduce the number of down times for manual adjustments and/or repairs of the cigarette rod making machine and/or of machines which supply various starting materials to and/or receive rod-shaped articles from a cigarette maker.

OBJECTS AND SUMMARY OF THE INVENTION

An object of the invention is to provide a novel and improved method of monitoring the density of a continuous stream of fibrous material and of evaluating and utilizing the results of the monitoring operation to enhance the quality of the ultimate product.

Another object of the invention is to provide a novel and improved method of rapidly ascertaining the density of a tobacco stream or the like with a heretofore unmatched degree of accuracy.

A further object of the invention is to provide a method which allows for a determination of density distribution in any selected direction within a stream of tobacco shreds or the like.

An additional object of the invention is to provide a method which can be used to alter any desired practical number of parameters that influence the appearance and/or other characteristics of plain or filter tipped cigarettes, cigarillos, filter rod sections and/or other rod-shaped smokers' articles or constituents of such articles.

Still another object of the invention is to provide a method which can be resorted to for the building of a highly satisfactory composite tobacco filler wherein a core containing a first fibrous material is surrounded by a tubular envelope consisting of a different second fibrous material.

Another object of the invention is to provide a method which, in addition to density measurement, can also serve for ascertainment of other characteristics of a moving stream of fibrous material, such as the orientation of particles in the stream, the length of such particles, the dimensions of the stream and/or others.

An additional object of the invention is to provide a method which can be used for simultaneous monitoring of a wide variety of identical or different characteristics of a moving stream of fibrous material, such as variations of the density in the direction of movement of the stream as well as at right angles to such direction.

A further object of the invention is to provide a method which renders it possible to influence the characteristics of a moving stream of fibrous material practically instantaneously upon detection of any departure of one or more characteristics from an optimum value.

An additional object of the invention is to provide a novel and improved apparatus which can be utilized for the practice of the above outlined method and to construct and assemble the apparatus in such a way that it can be installed in existing types of cigarette rod making and analogous machines for the making and/or processing of streams of fibrous material.

Another object of the invention is to provide an apparatus which can alter one or more characteristics of a moving tobacco stream with a degree f accuracy that cannot be matched by heretofore known apparatus.

A further object of the invention is to provide novel and improved density monitoring means for use in a cigarette rod making or like machine.

Still another object of the invention is to provide an apparatus which can regulate or correct the composition of a moving stream of tobacco shreds or other fibrous material practically immediately upon detection of departures from optimum composition so that the number of rejects is reduced to a fraction of rejects which are turned out by heretofore known apparatus.

An additional object of the invention is to provide an apparatus which can simultaneously monitor two or more characteristics of a moving tobacco stream in the longitudinal direction and also transversely of the moving stream.

A further object of the invention is to provide an apparatus which can monitor the characteristics of wrapped or unwrapped streams consisting of tobacco shreds or other fibrous material and which can be designed to apply the results of such monitoring in order to enhance the appearance, make-up and/or other desirable characteristics of the stream, of an intermediate product which contains the stream or of the ultimate product, such as plain or filter cigarettes, cigars, cigarillos or filter rod sections.

An additional object of the invention is to provide novel and improved means for evaluating signals denoting the density of a moving filler or stream consisting of or containing tobacco shreds or other fibrous material.

Still another object of the invention is to provide an apparatus which can ensure an optimal distribution of short tobacco or other types of lower-grade tobacco in a cigarette rod or the like.

An additional object of the invention is to provide the apparatus with novel and improved means for providing an image representing the distribution of density in a stream of tobacco or the like.

A further object of the invention is to provide an apparatus which can selectively influence the make-up of those portions of a moving tobacco stream which are most likely to influence the characteristics of the ultimate product.

An additional object of the invention is to provide a rod making machine which embodies the above outlined apparatus.

Another object of the invention is to provide the apparatus with novel and improved means for influencing the density, appearance, dimensions, weight and/or other characteristics of a stream of tobacco shreds or other fibrous material with a heretofore unmatched degree of reproducibility.

A further object of the invention is to provide an apparatus which can carry out qualitative and/or quantitative changes of a moving stream of fibrous material practically instantaneously as soon as the need for such changes arises.

Another object of the invention is to provide an apparatus which can build and process a stream consisting of or containing several types of fibrous material.

One feature of the invention resides in the provision of a method of forming and processing a stream of fibrous material, particularly a stream of tobacco particles for the making of plain cigarettes or other smokers' products. The method comprises the step of building a continuous stream including delivering fibrous material into an elongated path to thus form successive increments of the stream and moving the resulting stream along the path. Such stream building step is a function of a plurality of different parameters including the rate of delivery of fibrous material into the path, the dimensions of fibrous material and the orientation of fibrous material in the path. The method further comprises the steps of monitoring the density of the moving stream at a plurality of different distances from a reference plane which is at least substantially parallel to the direction of transport of the stream along the path, generating signals which denote the monitored density of the stream at such different distances from the reference plane, and varying (e.g., by one or more servomotors) one or more of the aforementioned and/or other parameters (which influence the appearance and/or the make-up of the stream) as a function of variations of at least one of the signals. The moving step preferably includes utilizing a moving conveyor to define at least a portion of the aforementioned path (the conveyor can constitute one wall of an elongated channel for fibrous material) and the delivering step then comprises supplying fibrous material to the conveyor. The supplying step preferably comprises conveying fibrous material in at least one current of air and directing the current of air against the conveyor. The moving step then preferably further comprises attracting fibrous material to the moving conveyor by suction. The reference plane is then defined by the moving conveyor, and the one parameter can be a parameter which determines (at least in part) the distribution of density in the stream. The varying step then includes varying such one parameter so as to establish a predetermined distribution of densities in the stream.

The delivering step can comprise accumulating the stream in the form of several longitudinally extending sections or strata whose characteristics can be influenced at least substantially independently of each other. The monitoring step then includes (or can include) separately ascertaining the density in each section or stratum of the stream, and the varying step then includes independently varying the parameters which determine or influence the densities of the respective sections or strata in dependency on variations of signals denoting the densities in the corresponding sections or strata so that the distribution of densities in the sections of the stream matches a predetermined pattern of densities (as considered at right angles to the reference plane). The accumulating step can include building the sections or strata seriatim in at least two (e.g., three) successive stages. For example, the accumulating step can include supplying to the path a first fibrous material during the first stage and a different second fibrous material during the next-following second stage. The varying step then includes varying the one parameter or two or more parameters in such a way that the composition of the stream matches a predetermined pattern (e.g., that one of the strata is thicker than the others, that one of the strata includes thicker and thinner portions, as considered in a direction at right angles to the reference plane), or that the density of the stream varies from stratum to stratum at a predetermined rate). Thus, the varying step can further include varying at least one of the aforementioned and/or other parameters so that the distribution of densities in the stream matches a predetermined pattern. Also, the supplying step can include feeding a first fibrous material (e.g., high-quality long shreds of tobacco leaf laminae) at a rate exceeding the rate at which a second fibrous material (e.g., surplus tobacco which was removed from the stream at an equalizing station) is supplied into the path. Such second fibrous material is supplied on top of the stream section or stratum which consists of or contains the first fibrous material.

As mentioned above, the delivering step can include supplying fibrous material to a moving conveyor in a current of air and the moving step can further include attracting the stream to the conveyor by suction. The reference plane is then defined by the conveyor (e.g., by one reach of an endless air-permeable belt conveyor) so that the monitoring step then includes ascertaining the density of the stream at a plurality of different distances from the conveyor including a range of distances nearest to the conveyor. The varying step then comprises (or can comprise) varying (as a function of variations of density within the aforementioned range of distances from the conveyor) at least one parameter which influences the density of a section or stratum of the stream nearest to the conveyor so that the distribution of densities in such stratum of the stream matches a predetermined pattern.

The delivering step can comprise supplying into the path fibrous material containing shreds of different lengths, and the varying step can comprise increasing the percentage of shorter shreds (e.g., surplus tobacco which was removed from the stream at a trimming station) when the monitored density of the stream decreases.

In accordance with a presently preferred embodiment of the invention, the monitoring step includes directing X-rays transversely across the stream so that at least some X-rays penetrate through the stream and the X-rays issuing from the stream in their entirety constitute an image denoting the distribution of density at the aforementioned different distances from the reference plane. The varying step then includes varying one or more parameters which influence the distribution of density and/or other characteristics of the stream so that the distribution matches a predetermined pattern. The signal generating step (including scanning of the image) can involve unidimensional linear scanning of the image and the monitoring step can further comprise pulsating the X-rays. If the image is a two-dimensional still image, such image is or can be indicative of the distribution of shreds in a stream of tobacco or the like. The signal generating step then preferably includes two-dimensional scanning of the image and the varying step can include varying a parameter which influences the stream building step as a function of detected orientation of shreds in the stream (e.g., for the purpose of changing the orientation so as to thereby influence the so-called fullness or hardness of the stream).

If the delivering and moving steps include using currents of air to supply fibrous material to and to retain such material in the aforementioned path, the varying step can include varying the quantity and/or the direction of air in such currents.

If the delivering step includes supplying fibrous material at a variable rate, the varying step can include varying such rate to thereby influence the density of the stream and especially the density of the filler which is obtained from the stream and is ready to be wrapped into a web of cigarette paper or the like. If the delivering step includes supplying fibrous material at a variable speed, the varying step can include varying the speed of fibrous material in the course of the supplying step to thereby vary the dimensions of the stream and the density of the filler. If the delivering step includes supplying into the path fibrous material in the form of shorter and longer shreds, the one (variable) parameter can include the ratio of shorter shreds to longer shreds in the fully built stream.

Another feature of the invention resides in the provision of an apparatus for forming and processing a stream of fibrous material, particularly a stream of tobacco particles for the making of cigarettes and analogous smokers' products. The apparatus comprises adjustable stream building means including a conveyor which (either alone or with stationary or mobile walls) defines an elongated path and means for supplying to the conveyor fibrous material which accumulates and forms a continuous stream thereon, means for monitoring the density of the stream at a plurality of different locations, as considered transversely of the path, including means for generating signals denoting the monitored density of the stream at the plurality of locations, and means for adjusting the stream building means in response to deviation of at least one of the signals from a preselected value. The signal generating means preferably comprises a so-called position sensitive detector, and the apparatus preferably further comprises signal evaluating means interposed between the detector of the monitoring means and the adjusting means.

The stream building means can comprise a plurality of components or parts each of which is constructed and arranged to form on the conveyor a separate stratum of the stream, and such strata include a first stratum which is directly adjacent to the conveyor. The adjusting means of such apparatus preferably comprises discrete adjusting elements (e.g., a battery of servomotors) for each of the components of the stream building means, and the evaluating means of such apparatus then comprises control means which serves to actuate each of the adjusting elements as a function of variations of signals denoting the densities of the respective strata. Each component can comprise a discrete adjustable device for supplying fibrous material and the adjusting elements are arranged to adjust the respective supplying devices. The evaluating means of such apparatus can comprise a discrete actuating arrangement for each of the adjusting elements.

The monitoring means preferably further comprises a source of X-rays and means for directing X-rays against the stream so that the radiation which penetrates through the stream of fibrous material impinges upon the position sensitive detector and forms thereon an image denoting the distribution of densities in the monitored portion (e.g., a complete cross-section) of the stream. The evaluating means of such apparatus comprises means for scanning the image and control means for transmitting to the adjusting means second signals denoting the densities of various portions of the stream. The detector can comprise an array of diodes, a CCD-array, an X-ray sensitive screen and a television camera for imaging X-rays onto the screen, or an X-ray amplifier. The detector may be a uni- or two-dimensional detector. The output or outputs of the control circuit (which forms part of or is combined with the evaluating means) are connected with the adjusting means.

The supplying means can comprise means (e.g., a duct with or without internal partitions) for delivering the fibrous material in at least one current of gaseous fluid (preferably air), and the adjusting means of such apparatus can comprise means for regulating at least one characteristic (such as the speed, direction of flow and/or quantity) of gaseous fluid.

If the supplying means comprises means for supplying at least two different types of fibrous material, the adjusting means can comprise means for regulating the quantity of one such type of fibrous material in the stream. For example, the one type of fibrous material may be reject tobacco which is removed from the fully grown stream by a preferably adjustable trimming or equalizing device downstream of the monitoring means.

Still further, the supplying means can comprise means for delivering fibrous material at a variable rate, and the adjusting means of such apparatus can include means for varying the rate of delivery of fibrous material, for regulating the speed of fibrous material on its way toward the conveyor and/or for adjusting the direction of delivery of fibrous material toward the conveyor.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 3 is a transverse vertical sectional view of the stream building unit in the apparatus of FIG. 1 and a diagrammatic view of the evaluating circuit which receives signals from the device for monitoring the density of the unwrapped tobacco stream;

FIG. 4 is a view as seen in the direction of arrows from the line IV—IV in FIG. 3;

FIG. 5 illustrates a twodimensional detector for use in the monitoring device which transmits signals to the evaluating circuit of FIG. 3;

DESCRIPTION OF THE PREFERRED EMBODIMENTS

Figure 1:
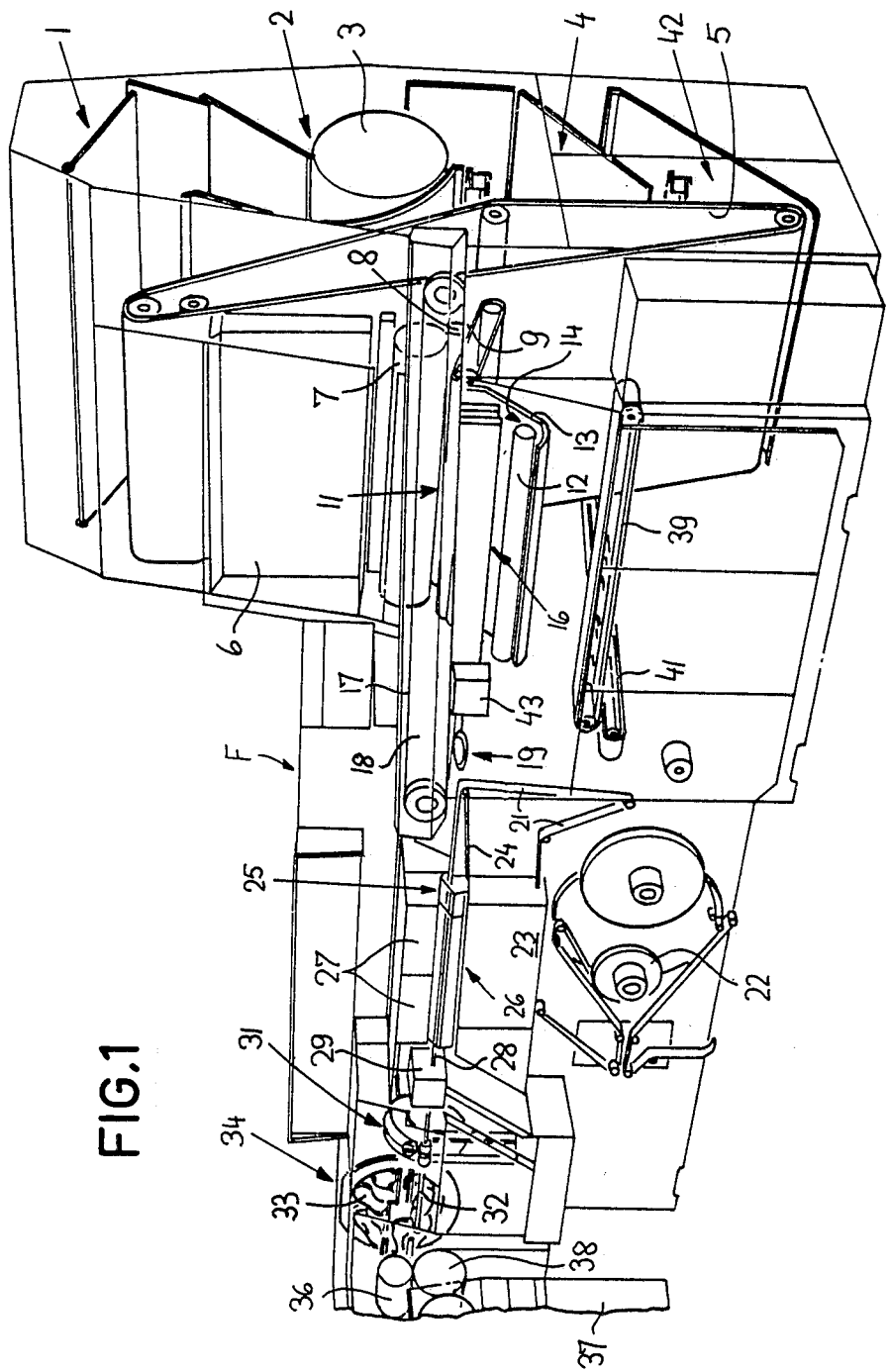
FIG. 1 is a perspective view of a cigarette rod making machine having an apparatus which embodies one form of the invention.

Referring first to FIG. 1, there is shown a cigarette rod making machine of the type known as PROTOS which is manufactured and sold by the assignee of the present application. The machine comprises a maine frame F wherein a gate 1 serves for intermittent delivery of batches of tobacco shreds to a first magazine 2 serving to accumulate and store a relatively large quantity of shreds. The bottom wall of the first magazine 2 is constituted by a rotary carded drum 3 which transfers tobacco shreds at a preselected rate into a second magazine 4 adjacent to the upwardly moving reach of an endless belt conveyor 5 having spaced-apart pockets (not specifically shown) for delivery of small batches of tobacco particles at a variable rate to an upright duct 6. The open lower end of the duct 6 is adjacent to a carded drum-type conveyor 7 which draws tobacco shreds at a uniform rate from the duct and moves past a rapidly driven picker roller 8 which transfers the shreds onto the upper reach of an endless apron conveyor 9 driven at a constant speed and serving to accumulate a rather wide carpet of tobacco shreds and to propel the leader of the carpet against a substantially vertical curtain of air which issues from the nozzle or nozzles of a tobacco classifying device 11. Heavier tobacco particles (such as fragments of ribs, birds' eyes and the like) penetrate through the curtain of air and accumulate in a suitable intercepting receptacle, but the curtain of air deflects all other tobacco particles into a funnel 14 which is bounded by a suitably curved stationary wall 13 and a carded conveyor 12. The carding of the conveyor 12 propels successive increments of the tobacco stream in the funnel 14 into an elongated path defined by a tobacco channel 16 whose bottom wall is the lower reach of an endless air-permeable belt conveyor 17 serving to accumulate a growing tobacco stream and to convey such stream lengthwise in a direction to the left, as viewed in FIG. 1. The heretofore described parts of the cigarette rod making machine are similar to or identical with those described and shown in greater detail in commonly owned U.S. Pat. No. 4,185,644 granted Jan. 29, 1980 to Uwe Heitmann et al. The disclosure of this patent is incorporated herein by reference.

The lower reach of the conveyor 17 is disposed immediately below the air-permeable bottom wall of an elongated suction chamber 18 which attracts the ascending tobacco shreds to the underside of the lower reach with a sufficient force to avoid uncontrolled shifting of shreds and to thus ensure a predictable building or growth of the stream as well as predictable movement of the stream with the conveyor 17 toward and past an adjustable trimming device 19 serving to remove the surplus from the underside of the fully grown stream and to thus convert the stream into a filler which is ready to be condensed and draped into a web 21 of cigarette paper. The web 21 is supplied by an expiring reel 22 and is advanced through an imprinting mechanism 23 by the upper reach of an endless belt conveyor 24 which transports it through a wrapping mechanism 26 of known design. Successive increments of the equalized tobacco stream advance beyond the left-hand end of the conveyor 17 and onto the web 21 on the upper reach of the conveyor 24 so that the web and the stream advance at the same speed. The wrapping mechanism 26 condenses the trimmed stream and drapes the web 21 therearound in such a way that one marginal portion of the web extends from the condensed stream and is coated with adhesive by a suitable paster 25 in a manner which is well known from the art of making cigarettes. The adhesive-coated marginal portion of the web 21 is thereupon folded over the other marginal portion to form therewith a seam which extends in parallelism with the axis of the resulting continuous cigarette rod 28. The seam is heated or cooled by a tandem sealer 27 (depending on the nature of adhesive which is applied by the paster 25).

The cigarette rod 28 advances through a density monitoring device 29 and thereupon passes through a cutoff 31 which subdivides the rod into a file of discrete plain cigarettes 32 of double unit length. Successive cigarettes 32 of the file are engaged by successive arms 33 of a rotary transfer device 34 which delivers the cigarettes to a drum 36 in a filter tipping machine 37. Successive cigarettes 32 are thereupon served on a drum-shaped conveyor 38 so that each cigarette 32 yields a pair of coaxial plain cigarettes of unit length. Such cigarettes are assembled with filter rod sections of double unit length to form filter cigarettes of double unit length. The filter tipping machine 37 may be of the type known as MAX or MAX S, both manufactured and sold by the assignee of the present application.

Conveyor belts 39 and 41 are used to transport the removed surplus tobacco from the trimming device 19 into a third magazine 42 for introduction into the pockets of the conveyor 5. The magazine 42 is immediately adjacent to the upwardly moving run of the conveyor 5 at a level below the magazine 4.

FIG. 1 further shows a monitoring device 43 which is mounted upstream of the trimming device 19 adjacent to the unequalized stream of tobacco shreds. In accordance with a feature of the invention, the monitoring device 43 comprises a source of X-rays which are caused to travel across the path of movement of the untrimmed tobacco stream. The monitoring device 43 further comprises a transducer which is located in the path of X-rays that have penetrated through the running tobacco stream and forms a density image of the stream. The transducer is a so-called position sensitive transducer capable of forming a density image which is indicative of the density of the tobacco stream at different distances from the (reference) plane of the lower reach of the conveyor 17. If desired, the aforementioned monitoring device 29 can be constructed and assembled in the same way, i.e., it can also comprise a source of X-rays and a transducer capable of forming an image of the X-rays which have penetrated through the rod-like filler of the wrapped tobacco stream (i.e., through the cigarette rod 28).

Figure 2:
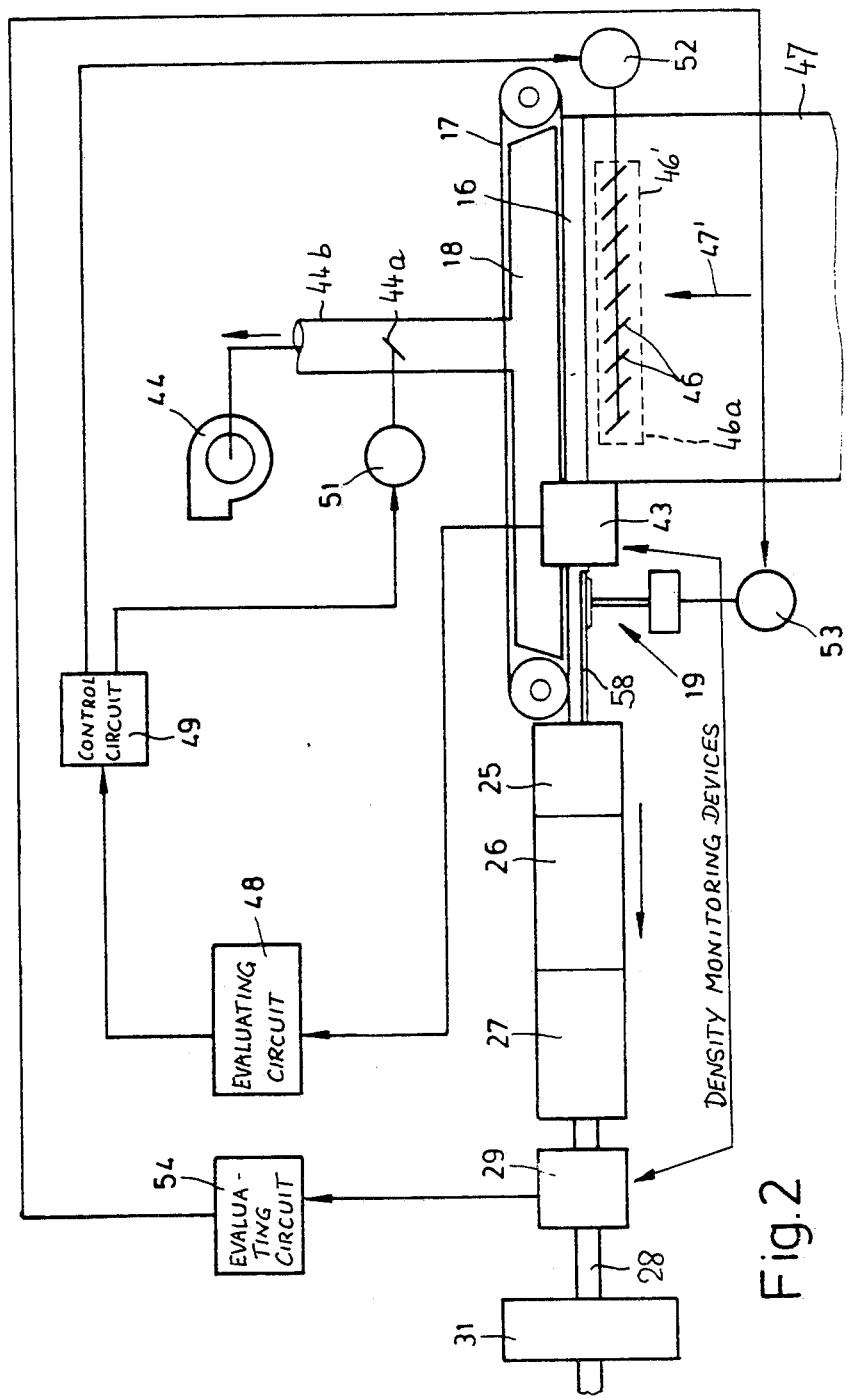
FIG. 2 is an enlarged diagrammatic view of the stream building unit in the apparatus of FIG. 1 and of the means for evaluating and utilizing the signals denoting the density of various layers of the untrimmed tobacco stream and the density of the filler of a continuous cigarette rod.

FIG. 2 shows the details of a portion of the cigarette rod making machine of FIG. 1, namely the parts including the two density monitoring devices 29, 43, the conveyor 17 and the means which cooperate with the conveyor 17 to build thereon a continuous tobacco stream 58. The lower reach of the conveyor 17 is the bottom wall of the tobacco channel 16 which receives tobacco shreds from a duct 47 in the direction indicated by the arrow 47'. The suction chamber 18 at the upper side of the lower reach of the conveyor 17 is connected with the suction intake of a blower 44 or another suitable suction generating device. Suction in the chamber 18 is sufficiently pronounced to attract the tobacco shreds which ascend in the direction indicated by the arrow 47' as well as to attract the growing tobacco stream and the fully grown tobacco stream at the underside of the lower reach of the conveyor 17. The rate of air flow through the interstices of the conveyor 17 and through the bottom wall of the suction chamber 18 can be adjusted by a valve 44a in a conduit 44b leading from the suction chamber 18 to the intake of the blower 44. The means for adjusting the position of the valve 44a, and hence the rate of air flow through the conveyor 17, comprises a servomotor 51 which receives appropriate signals from the transducer of the density monitoring device 43.

The lower portion of the tobacco channel 16 or the upper portion of the duct 47 has inclined slots 46 which permit currents of air to enter at a selected angle with reference to the plane of the lower reach of the conveyor 17 and to thus impart to the ascending tobacco shreds a more or less pronounced component of movement in the direction of travel of the tobacco stream 58 from the stream building station toward the trimming device 19. The reference character 46' denotes a source of gaseous fluid which admits currents of air into the slots 46. The currents of air which enter the channel 16 via slots 46 assist the ascending tobacco shreds in their movement toward the underside of the lower reach of the conveyor 17. The slots 46 are defined by a series of louvers or vanes 46a whose inclination is adjustable by a second servomotor 52 indirectly receiving appropriate signals from the density monitoring device 43. The louvers 46a serve to adjust the inclination of slots 46 and/or the rate of flow of air through such slots. The manner in which currents of air can be admitted into a shower of ascending tobacco shreds is fully disclosed in commonly owned U.S. Pat. No. 4,175,570 granted Nov. 27, 1979 to Uwe Heitmann. The disclosure of this patent is incorporated herein by reference.

The output of the monitoring device 43 is connected with the input of an evaluating circuit 48 whose output is connected to a control circuit 49 for the aforementioned servomotors 51 and 52. The signals which are generated and transmitted by the control circuit 49 are indicative of density in different layers or strata of the tobacco stream 58 ahead of the trimming device 19 and are used to vary certain parameters (namely, the rate of flow of air currents through the air-permeable conveyor 17 and the inclination of air currents which enter the channel 16 via slots 46) which determine the characteristics of the tobacco stream 58 moving into the range of the cutter or cutters of the trimming device 19. The servomotor 51 varies the rate of air flow through the conveyor 17, and the servomotor 52 varies the rate and/or the direction of flow of currents of air through the slots 46. The output of the control circuit 49 can be connected to further adjusting means which can vary one or more parameters that determine the composition and/or other features of the tobacco stream and/or of the products which contain portions of such stream. For example, the output of the control circuit 49 can be further connected with an ejector of the type disclosed in commonly owned U.S. Pat. No. 4,177,670 granted Dec. 11, 1979 to Uwe Heitmann et al. so that the ejector segregates cigarettes 32 containing fillers whose density is outside of a range of acceptable densities. The disclosure of this patent is incorporated herein by reference. As a rule, or at least in many instances, segregation of defective rod-shaped articles will take place in the filter tipping machine 37.

The density monitoring device 29 is connected with an evaluating circuit 54 whose output is connected with means (such as the schematically illustrated servomotor 53) for adjusting the level of the knife or knives of the trimming device 19, i.e., for removing a larger or smaller quantity of surplus tobacco from the unequalized tobacco stream 58 so that the filler of the cigarette rod 28 will contain a larger or smaller quantity of tobacco shreds. This directly affects the density of fillers in the cigarettes 32 because the wrapping mechanism 26 converts the trimmed stream 58 into a rod-like filler of predetermined diameter irrespective of the quantity of tobacco shreds per unit length of the trimmed stream.

It is further clear that the output of the control circuit 54 can be connected with an ejector for defective cigarettes 32 or for rod-shaped articles which embody such cigarettes or portions of such cigarettes. Thus, defective or unsatisfactory sections of the trimmed tobacco stream can be ejected in response to signals which are generated by the monitoring device 43 or by the monitoring device 29. As mentioned above, the monitoring device 29 can also comprise a source of X-rays and a transducer capable of forming an image from those X-rays which have penetrated through the filler of the wrapped cigarette rod 28.

FIG. 3 shows the details of the density monitoring device 43 and of the evaluating circuit 48. The airpermeable bottom wall of the suction chamber 18 above the lower reach of the conveyor 17 is shown at 56. The tobacco stream 58 is formed at the underside of the lower reach of the conveyor 17 between the sidewalls 40 or cheeks 57 of the tobacco channel 16. The source 59 of X-rays is disposed at one side of the channel 16 and the beam 62 of X-rays is directed against the respective side of the fully grown stream 58. The source 59 can constitute a conventional X-ray tube and the beam 62 passes first through the aperture 63' of a first collimating diaphragm 60', and thereupon through one of the sidewalls 57 and into the tobacco stream 58. That portion of radiation which penetrates through the entire tobacco stream 58 thereupon passes through the other sidewall 57 and through the aperture 63 of a second collimating diaphragm 60 prior to impinging upon the detector or transducer 61 of the monitoring device 43.

By way of example, the source 59 can comprise a tungsten anode and can be operated at a potential of between 14 and 20 kilovolts. The sidewalls 57 of the tobacco channel 16 are permeable to X-rays and may consist of thin titanium sheets. They can be said to constitute windows which permit practically unimpeded passage of X-rays. The transducer 61 is an X-ray detector, preferably a unidimensional array of diodes or a CCD-array, i.e., a charge-coupled semiconductor arrangement. A suitable diode array is manufactured and sold by EG & G Instruments GmbH, München, Federal Republic Germany, under the catalog number RL 1024 SFX. The utilization of such detector contributes to simplicity of the apparatus. A suitable CCD-array is manufactured by the Fairchild Corporation, e.g., an array known as Line Scan Image Sensor type CCD 143 DC. The arrangement is such that the radiation which has penetrated through the tobacco stream 58, the lefthand sidewall 57 of FIG. 3 and the aperture 63 of the diaphragm 60 produces a stream image which is indicative of the distribution of density in various layers or strata of the stream 58. Such image is scanned along a line 81 (see FIG. 4) which extends vertically, as viewed in FIGS. 3 or 4, i.e., which is normal to the plane of contact between the underside of the lower reach of the conveyor 17 and the upper side of the fully grown tobacco stream 58. In other words, appropriate scanning of the stream image 71 in or on the transducer 61 of the monitoring device 43 renders it possible to ascertain the density of the stream 58 at different distances from a reference plane which, in the embodiment of FIGS. 3 and 4, is the plane of the underside of the lower reach of the conveyor 17. If the manufacturer wishes to obtain information pertaining to the structure of the tobacco stream 58, the composition of certain portions or sections of the stream, the orientation of shreds in the stream and/or the length of tobacco shreds which constitute the stream, the transducer or detector 61 is a twodimensional (planar) diode array, a CCD-array (matrix) or an X-ray image screen. Each of these detectors allows for a twodimensional evaluation of the stream image such as is necessary to ascertain certain characteristics of the stream 58.

The circuit 48 evaluates the information which is furnished by the stream image 71 in or on the transducer 61. This circuit 48 comprises a scanning circuit 50 (e.g., a circuit of the type known as RC 1024 SA which is manufactured and sold by RETICON-EG & G Instruments, München, Federal Republic Germany) which scans the stream image at a perselected frequency by scanning the discrete bits or lines of information and a first output of which transmits appropriate electric signals. Such output is connected to the input of a voltage-frequency converter 65 whose output is connected with the input of a first counter 64. The scanning circuit 50 has a second output which is connected with the input of a pulse counter 66 serving to count the number of scans which are carried out by the circuit 50 and whose output is also connected with the counter 64. The signals which appear at the output of the counter 64 are transmitted to the input of the aforementioned control circuit 49 for the servomotors 51 and 52. The control circuit 49 comprises a digital-analog converter 67 which is directly connected with the output of the counter 64 and whose output is connected with one input of a comparator 68. Another input of the comparator 68 receives a reference signal from a suitable source 69. The output of the comparator 68 transmits a signal when the intensity or another characteristic of the analog signal furnished by the converter 67 deviates from the same characteristic of the reference signal which is furnished by the source 69. As explained in connection with FIG. 2, analog signals which are transmitted by the output of the comparator 68 (i.e., by the output of the control circuit 49) are transmitted to the servomotor 51 and/or 52 (and/or one or more additional servomotors) to vary one or more selected parameters which influence the characteristics of the tobacco stream 58.

In lieu of being connected with the counters 64 and 66, the evaluating circuit 50 can transmit signals to the input of an analog-digital converter 65' (by way of conductor means 72) whose output transmits signals to a modified control circuit 49'. Such switch from transmission of signals to the control circuit 49 to transmission of signals to the control circuit 49' will take place when it is desired to depart from an integrating evaluation of signals which are transmitted by the circuit 48. The purpose of the control circuit 49' is to transmit signals which are obtained by a localized (position sensitive) resolution of signals obtained from the evaluating circuit 48. The second control circuit 49' comprises a first memory 74 which is connected with the output of the converter 65' and whose output is connected with one input of a comparator 77. The number of bits of information which can be stored in the memory 74 corresponds to the number of bits of information which the transducer 61 of the monitoring device 43 receives per cross-section of the tobacco stream 58. A second memory (reference memory) 76 contains as many bits of information as the memory 74 and is connected with a second input of the comparator 77. The purpose of the comparator 77 is to compare each bit of actual information (stored in the memory 74) with the corresponding bit of information stored in the reference memory 76 and to transmit signals whenever two bits of information are dissimilar. The signals at the output of the comparator 77 are used for regulation of one or more adjusting means (e.g., servomotors), either directly or after conversion in a suitable digital-analog converter 77a.

As mentioned above, FIG. 4 shows a line 81 representing a row of diodes which form part of a unidimensional diode or CCD-array 79. The direction of travel of the tobacco stream 58 with the lower reach of the conveyor 17 is indicated by the arrow 78. The row 81 of diodes extends at right angles to the plane of the lower reach of the conveyor 17 and at right angles to the direction which is indicated by the arrow 78. The dimensions of the stream image 71 are determined by the dimensions of the aperture 63 in the diaphragm 60.

FIG. 5 shows a twodimensional diode or CCD-matrix 79' which comprises a planar arrangement of several neighboring parallel rows 81' of diodes. Such matrix is preferably used when the source of radiation emits pulsating X-rays which can produce a two-dimensional stream image.

Referring again to FIG. 2, the evaluating circuit 54 preferably contains a scanning circuit which is identical with the circuit 50 of the evaluating circuit 48. Alternatively, the circuit 54 may be a well known SMR unit which can also furnish appropriate signals for the servomotor 53 or for one or more additional adjusting means for varying one or more parameters which influence or determine the characteristics of the tobacco stream 58. If the monitoring device 43 comprises an X-ray image amplifier, such amplifier may be of the type known as RBV 1712 with camera (manufactured and distributed by Siemens AG, München, Federal Republic Germany).

The mode of operation of the system which is shown in FIGS. 2, 3, 4 and 5 is as follows:

The stream 58 is built on the conveyor 17 in the channel 16 at a level above the duct 47. The growing stream and the fully grown stream advance with the lower reach of the conveyor 17 in the direction of arrow 78. The X-ray tube 59 emits the beam 62 of X-rays which are collimated by the diaphragms 60', 60 and pass through the unequalized tobacco stream 58 upstream of the trimming device 19 to form an image 71 on the diode array 79. The dimensions of the image 71 are determined by those of the aperture 63 in the diaphragm 60. The array 79 of FIG. 4 is assumed to comprise a row 81 of 1024 diodes and, as mentioned above, this row extends at right angles to the direction of movement of the stream 58 (as indicated by the arrow 78). The intensity distribution in the stream image 71 corresponds exactly to distribution of density in the tobacco stream 58. By measuring the intensity of X-rays which impinge upon discrete diodes of the row 81, one can obtain a density profile of the stream as measured at different levels below the lower reach of the conveyor 17, i.e., as considered in the direction of the height of the stream. Each measuring operation involves an irradiation stage and a scanning stage. During the irradiation stage, the X-rays penetrate through the stream 58 and form an image on the diode array 79. Depending on the circumstances, the irradiation stage can last between 10 and 500 milliseconds. During the next-following scanning stage, the circuit 50 of the evaluating circuit 48 ascertains seriatim the intensity of voltage signals which are generated by the diodes of the row 81 and denote the density in the corresponding layers or strata of the stream 58. The scanning preferably begins in immediate proximity of the lower reach of the conveyor 17 and proceeds from diode to diode of the row 81 toward the exposed underside of the fully grown but still unequalized tobacco stream 58. The intensity of signal which is stored by each of the 1024 diodes in the row 81 corresponds to intensity of radiation to which the respective diode was exposed during the preceding irradiating stage. The scanning takes place at the selected frequency, e.g., 300 kilohertz, so that each scanning stage (involving a single scanning of each diode in the row 81) takes up approximately ten milliseconds. Each of the scanned diodes furnishes a discrete voltage signal which is indicative of intensity of radiation to which the respective diode was subjected prior to scanning. Since the X-rays penetrate the stream 58 along straight paths, each of the thus obtained signals denotes the density of the stream 58 at the corresponding distance from the plane of the underside of the lower reach of the conveyor 17, namely, the distance between such reference plane and the scanned diode. Thus, the diode array 79 provides for a local (position sensitive) resolution of the information which is contained in its diodes to provide data pertaining to density of the stream 58 differentiated according to the distance from the lower reach of the conveyor 17.

The voltage signals which are furnished by the diodes of the row 81 during each scanning stage are supplied to the voltage-frequency converter 65 which converts such signals into sequences of impulses transmitted to the corresponding input of the first counter 64. The number of impulses in each sequence corresponds to the intensity of signal from one of the diodes and hence to density of the stream 58 at a particular distance from the lower reach of the conveyor 17. Each series of impulses is generated within the respective scanning stage. The number of impulses in each series within a scanning stage is a function of the intensity of signal which is furnished by the respective diode of the row 81; this is the result of transmission of signals from the scanning circuit 50 to the voltage-frequency converter 65.

As mentioned above, the output of the scanning circuit 50 can transmit signals to the second control circuit 49' via conductor means 72 and analog-digital converter 65'. Such signals are admitted into and stored in the memory 74. The comparator 77 addresses the memory 74 to compare each of the 1024 stored signals with the corresponding reference signal in the second memory 76, and the comparator 77 transmits control signals whenever the signals which are stored in the memory 74 deviate from the corresponding reference signals in the memory 76. The comparator 77 can constitute a commercially available microcomputer. The signals at the output of the comparator 77 can be used to vary one or more parameters which determine the characteristics of the tobacco stream 58. For example, and as shown in FIG. 2 (it being now assumed that the control circuit 49 of FIG. 2 or 3 is replaced with the control circuit 49'), the signals at the output of the comparator 77 can influence the servomotor 51 to thereby regulate suction in the chamber 18 above the lower reach of the conveyor 17 and/or the rate of air flow through the slots 46 and/or the direction of air flow through such slots. Furthermore, an additional servomotor can influence the speed of the conveyor 5, of the carded conveyor 7 and/or another conveyor which, by changing its speed, can influence the rate of admission of tobacco particles into the duct 47 and thence into the tobacco channel 16. Still further, the signals at the output of the comparator 77 can influence the speed of the carded conveyor 12 and hence the velocity of tobacco particles which are propelled into the duct 47 and thence into the channel 16 to form the stream 58 at the underside of the lower reach of the conveyor 17.

If the unidimensional diode array 79 of FIG. 4 is replaced with the twodimensional (planar) matrix 79' of FIG. 5, the evaluation of information which is stored in the thus obtained stream image can be utilized to ascertain the structure of the stream 58 as well as the orientation of shreds in such stream. For example, such information can lead to detection of clumps or clusters of interlaced tobacco shreds which are sufficiently large to cause the so-called stoppers, i.e., clogging of the channel 16 and lengthy interruptions in operation of the cigarette rod making machine. It should be borne in mind that a modern cigarette maker can turn out up to and even well in e access of 8000 cigarettes per minute so that the losses in output of such machines are extremely high, even if their operation is interrupted for very short intervals of time. The losses are compounded due to the fact that, as a rule, a modern cigarette rod making machine forms part of a large production line including one or more filter rod making machines, one or more filter tipping machines and one or more tobacco packing machines. In many instances, interruptions of operation of one of these machines entail or necessitate immediate or rapidly following stoppage of one or more additional machines or complete stoppage of the entire production line.

Instead of transmitting signals via conductor means 72 and analog-digital converter 65', the scanning circuit 50 in the evaluating circuit 43 can transmit signals to the counter 64 via voltage-frequency converter 65. The counter 64 totals the impulses of several successive series of impulses or of all series of impulses within a scanning stage. The number of impulses or impulse series which are to be totalized by the counter 64 is determined by the setting of the second counter 66 which is connected to an output of the scanning circuit 50 and counts the number of scans. This renders it possible to ascertain the densities of selected strata of the tobacco stream 58, e.g., the density of the stratum which is immediately adjacent to the underside of the lower reach of the conveyor 17. Thus, the counter 66 can cause the counter 64 to transmit to the digital-analog converter 67 a signal after the scanning circuit 50 has completed the scanning of a certain number of diodes in the row 81, e.g., a number of diodes storing signals which denote the density of different substrata of the first or uppermost stratum of the tobacco stream 58 at the underside of the lower reach of the conveyor 17. The counter 64 interrupts the count whenever it receives a signal from the counter 66, and the output of the counter 64 then transmits a signal corresponding to the integral of density of the freshly monitored stratum of the stream 58. The thickness of such stratum can be selected by adjusting the counter 66 accordingly. For example, the setting of the counter 66 can be such that the output of the counter 64 transmits a signal upon completed scanning of the first or uppermost 400 diodes in the row 81 of the diode array 79 shown in FIG. 4. If the overall height of a fully grown tobacco stream 58 is approximately 10 mm, the thickness of the uppermost stratum whose density is monitored by the 400 uppermost diodes of the row 81 equals or approximates 4 mm. The evaluating circuit 48 can be designed to enable the counter 64 to transmit signal denoting the integrated density of any selected stratum of the tobacco stream 58, e.g., a stratum nearest to the conveyor 58, a stratum which is remotest from the conveyor 17, or any one of a practically infinite number of intermediate strata. All that is necessary is to properly set the counters 64 and 66, i.e., that the counter 64 begins to totalize the series of impulses starting with the n-th series and that the counter 66 causes the counter 64 to transmit a signal to the converter 67 upon completed totalizing of m series of impulses (in theory, n can be any number between zero and 1023, and m can be any number between 1024 and zero). Since the diodes of the row 81 are or can be equidistant from one another, it is rather simple to determine the distance between the selected stratum of the tobacco stream 58 and the underside of the lower reach of the conveyor 17 as well as the thickness of the selected stratum. Thus, the apparatus of the present invention allows for predictable and accurate monitoring of the density of an entire tobacco stream or of any selected layer or stratum of such stream.

The signal which is transmitted by the output of the counter 64 (in response to a signal from the counter 66) is converted into an analog signal by the converter 67 and is transmitted to the corresponding input of the comparator 68 which compares it with the corresponding reference signal from the source 69. If the analog signal from the converter 67 deviates from the corresponding reference signal, the output of the comparator 68 transmits a signal which can be used in a manner as described with reference to FIG. 2, i.e., to vary one or more parameters which determine the charactistics of the tobacco stream 58 via servomotor 51 and/or 52 and/or one or more additional adjusting means. As a rule, the adjustment will involve a regulation of the rate of air flow in the duct 47, of the direction of air flow through the slots 46, and/or of the speed of air flow through the slots 46; the quantity of delivered fibrous material and/or the speed and/or the direction of delivery of fibrous material; the percentage of discard or surplus or short tobacco (supplied by the conveyors 39, 41 to the magazine 42 from the trimming device 19); and/or the pressure in the suction chamber 18. By properly regulating one or more of these parameters, one can build a tobacco stream which is incomparably superior to tobacco streams which are formed in presently known stream building apparatus.

Figure 6:
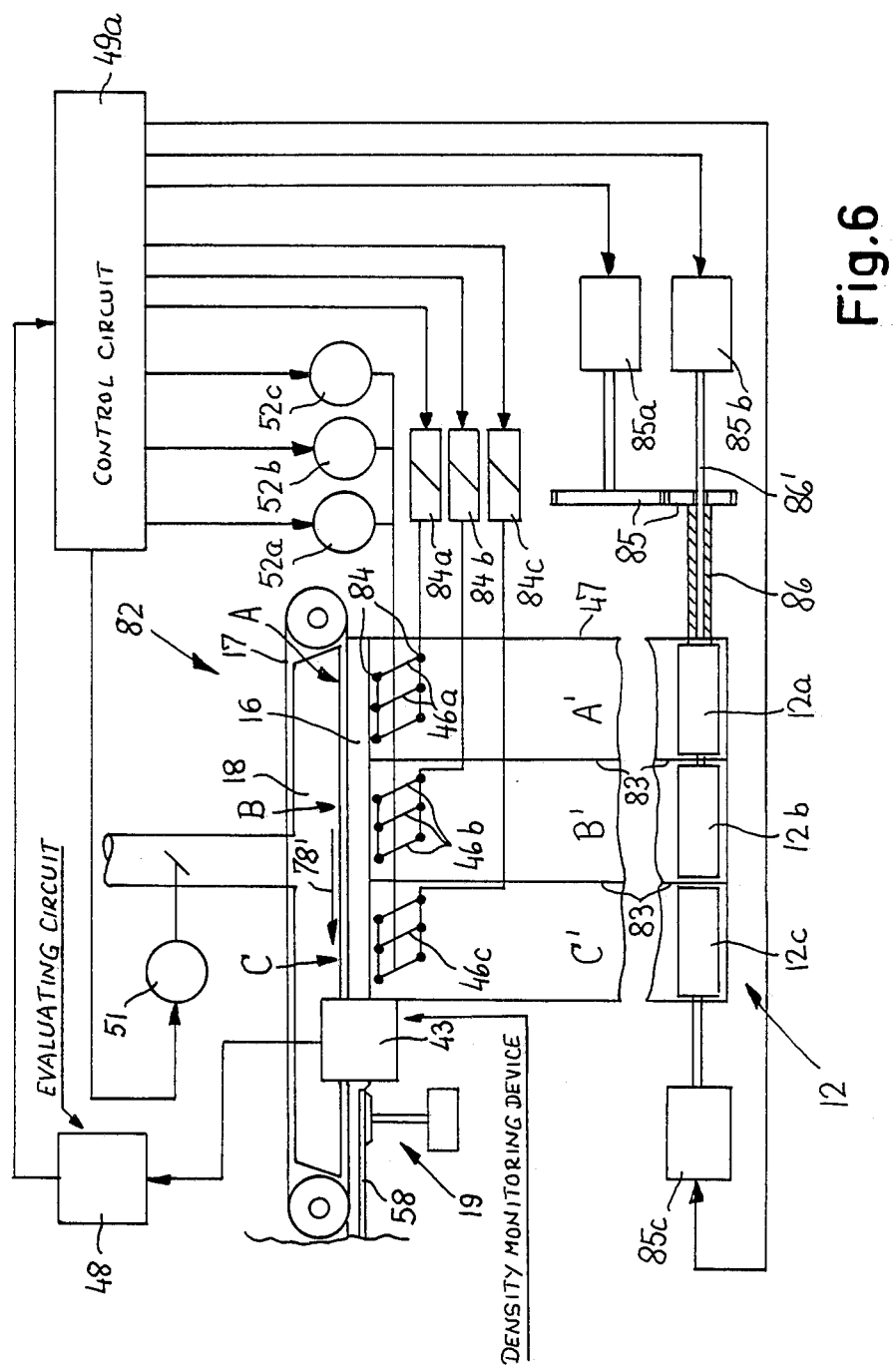
FIG. 6 is a schematic view similar to that of FIG. 2 but showing a modified stream building unit and a modified evaluating circuit with associated adjusting means.
Figure 9:
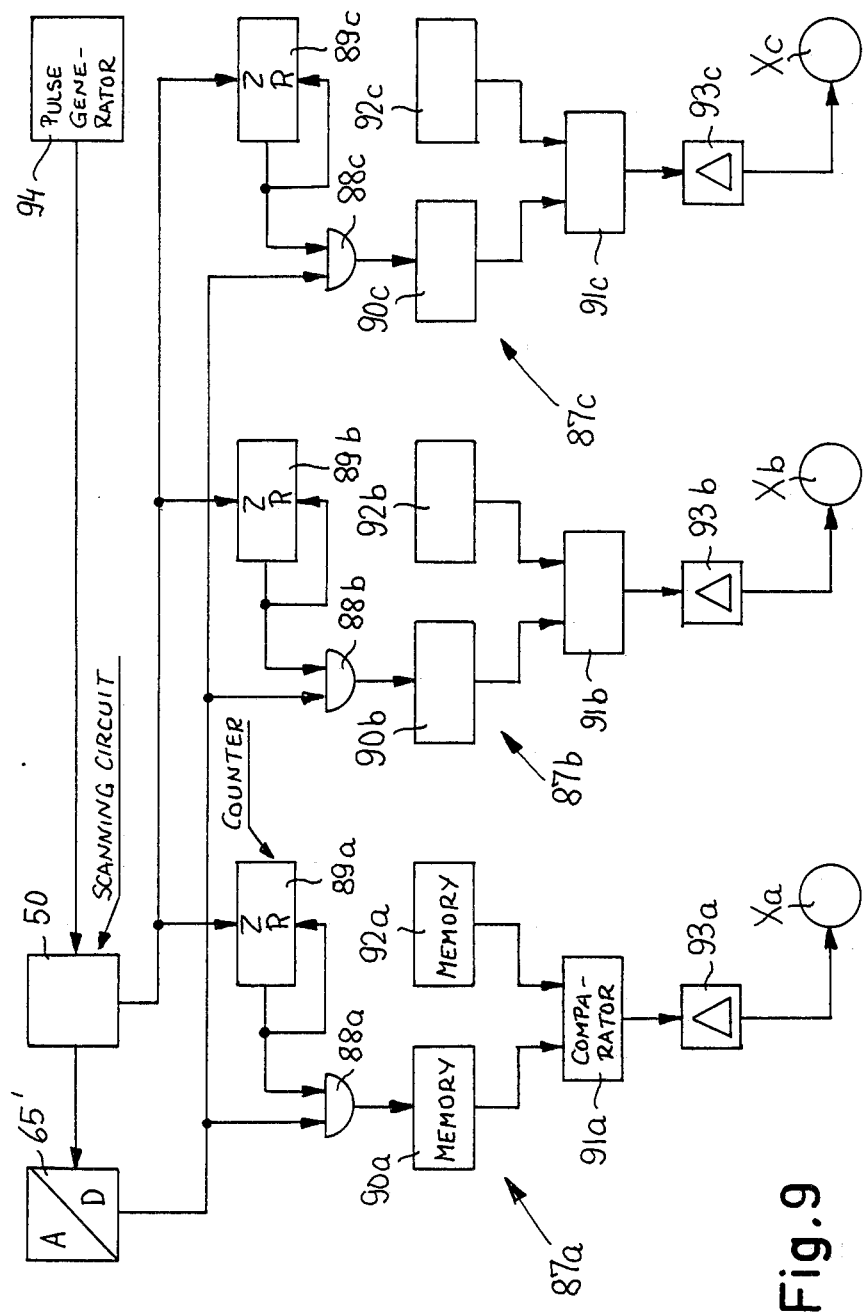
FIG. 9 illustrates the details of the evaluating circuit which is shown in FIG. 6.

FIGS. 6 and 9 illustrate a presently preferred second embodiment of the improved apparatus. All such parts which are identical with or clearly analogous to the corresponding parts of the apparatus of FIGS. 2 to 5 are denoted by similar reference characters.

In FIG. 6, the reference character 82 denotes the adjustable stream building unit of a cigarette rod making machine. The unit 82 includes a tobacco duct 47 wherein a current of air transports discrete tobacco shreds toward the underside of the lower reach of an air-permeable belt conveyor 17. The lower reach of this conveyor is the bottom wall of the tobacco channel 16 and such lower reach advances along the air-permeable bottom wall of the stationary suction chamber 18. The tobacco stream 58 advances past a density monitoring device 43 and thereupon into the range of a trimming device 19 which removes the surplus. Suction in the chamber 18 suffices to attract the particles of tobacco in the actual stream building zone above the duct 47 as well as to attract the fully grown tobacco stream 58 so that the latter shares the movement of the lower reach of the conveyor 17. The direction of movement of the tobacco stream 58 with the lower reach of the conveyor 17 is indicated by the arrow 78'.

The duct 47 contains two partitions 83 which subdivide its interior into three discrete passages or channels A', B' and C' which render it possible to carry out a three-stage buildup of the tobacco stream 58, namely, in the components or parts A, B and C of the unit 82. Each of the passages or channels A', B', C' receives currents of air through at least one set of louvers or vanes 46a, 46b, 46c, respectively. Such louvers are provided in at least one wall of the respective channel. The louvers 46a, 46b and 46c are adjustable so that they can regulate the orientation of the currents of air which enter the channels A', B', C' by way of the slots between the respective louvers. The reference characters 84 denote pivots for the louvers 46a, 46b, 46c, and these louvers are respectively movable with reference to the corresponding pivots 84 by three adjusting means in the form of servomotors 84a, 84b, 84c. Such pivotability of the louvers 46a-c allows for changes in the orientation of currents of air which enter the respective channels A', B', C'.

The rate of admission of air by way of the slots between the louvers 46a, 46b, 46c is respectively regulatable by adjusting means in the form of servomotors 52a, 52b, 52c. For the sake of simplicity, FIG. 6 merely shows a single conduit 52A which leads from the servomotors 52a-52c to the slots of the three channels A', B', C'; in actual practice, each of the servomotors 52a-52c controls the rate and speed of air flow in a discrete conduit or set of conduits.

The carded conveyor 12 of FIG. 6 comprises three coaxial tobacco supplying portions or components 12a, 12b, 12c which respectively serve to propel tobacco shreds at a variable rate and/or speed into the adjacent channels A', B', C'. Each of the conveyor portions 12a, 12b, 12c can be rotated by a separate drive 85a, 85b, 85c, respectively. The drive 85a transmits torque to the conveyor portion 12a by way of a gear train 85 and a hollow shaft 86. The conveyor portion 12b receives torque from the corresponding drive 85b by way of a shaft 86' which extends through the hollow shaft 86. The output shaft of the drive 85c is directly coupled to the conveyor portion 12c.

The servomotors 52a-52c, 84a-84c and 85a-85c receive signals from the output of the control circuit 49a which is or can constitute a part of the evaluating circuit 48. The input of the evaluating circuit 48 is connected to the output of the density monitoring device 43 which has a position sensitive detector serving to generate signals which are thereupon evaluated by the circuit 48. The details of the control circuit 49a are shown in FIG. 9. As already explained with reference to FIG. 3, the scanning circuit 50 transmits to the analog-digital converter 65' signals denoting the density profile of the tobacco stream 58, and such signals are converted into series of digital signals. The digital signals are transmitted to the corresponding inputs of three identical actuating circuit arrangements 87a, 87b and 87c. The input of each of the actuating arrangements 87a-87c is one input of an AND gate (88a, 88b, 88c) which is connected with the output of the analog-digital converter 65'. The second inputs of the AND gates 88a, 88b, 88c are respectively connected with the outputs of counters 89a, 89b, 89c, and the outputs of these counters are further connected to the corresponding reset inputs R. The counting inputs of the counters 89a-89c are connected with the pulse generating output of the scanning circuit 50.

The outputs of the AND gates 88a-88c are respectively connected with the inputs of memories 90a, 90b, 90c. The number of bits of information which can be stored in the memories 90a-90c matches the number of bits stored in the detector of the monitoring device 43. The outputs of the memories 90a-90c are connected to the corresponding inputs of three comparators 91a, 91b, 91c each of which has a second input connected to the corresponding reference memory 92a, 92b, 92c. Each of the memories 92a-92c contains the same number of bits of information as the associated memory 90a, 90b, 90c, respectively. The outputs of the comparators 91a, 91b, 91c transmit signals which denote the differences between the respective signals from the memories 90a-92a, 90b-92b and 90c-92c to amplifiers 93a, 93b, 93c which, in turn, transmit signals to the corresponding adjusting elements Xa, Xb, Xc. These adjusting elements can respectively constitute the servomotors 52a-52c and/or 84a-84c and/or 85a-85c and/or other servomotors which serve to vary one or more parameters that determine the characteristics of the tobacco stream 58.

Figure 8:
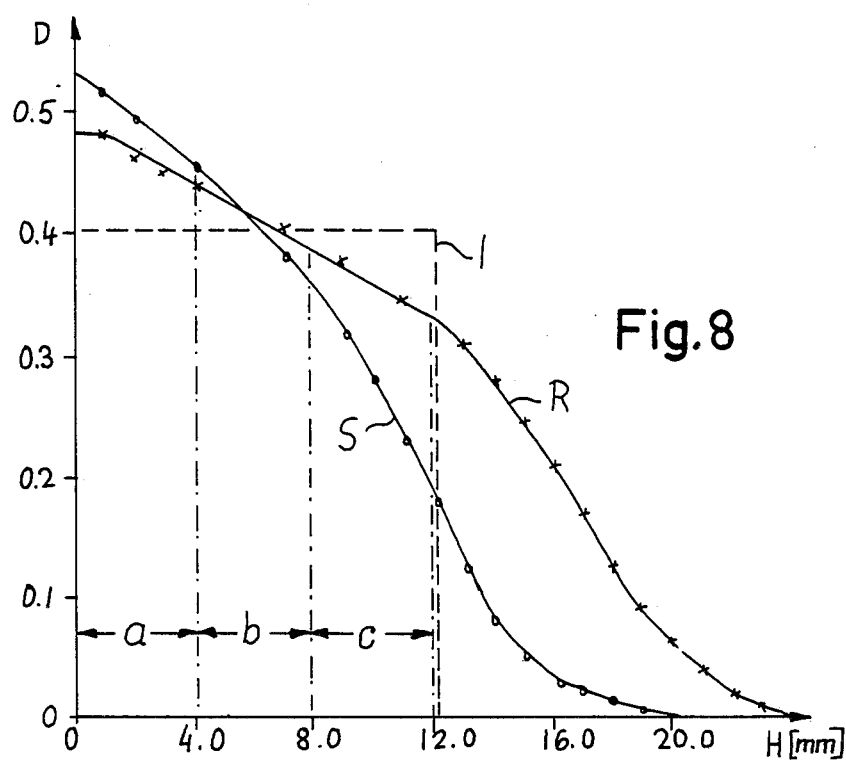
FIG. 8 is a graph showing the ideal and other density profiles of a tobacco stream.

The mode of operation of the apparatus of FIGS. 6 and 9 will be explained with reference to FIG. 8 which shows the density profile of one cross-section of the unwrapped tobacco stream 58. The density D is measured (in relative units) as a function of the distance H (in millimeters) from the reference plane (the plane of the underside of the lower reach of the conveyor 17 shown in FIG. 6). The broken-line curve I denotes the ideal progress of density along the full height of the tobacco stream 58, i.e., a distribution of density which cannot or is rather unlikely to be achieved in actual practice. Ideal density is uniform across the entire cross-section of the tobacco stream 58 and drops to zero abruptly at the periphery of the stream. An object of the invention is to ensure that the actual density will approximate the ideal density as closely as possible. The curve R of FIG. 8 denotes a progress of density which comes rather close to the ideal curve I. The most important part of the density curve is that which denotes the density of the stratum a that is immediately adjacent to the lower reach of the conveyor 17, i.e., within a distance corresponding to the thickness of that tobacco layer a which is obtained from shreds supplied by the channel A' of the duct 47. An equally or almost equally important part is that of the stratum c obtained from the tobacco shreds which are supplied by the channel C' of the duct 47. The thickness of this stratum in the graph of FIG. 8 is the same or nearly the same as that of the stratum a or a median stratum b. The density in the stratum a exerts a pronounced influence upon the density of the stratum c. Thus, if the density of the stratum a is excessive, the density of the stratum or strata (b and/or c) which is or are located at a greater distance from the conveyor 17 is unsatisfactory. This will be readily appreciated since a relatively dense stratum a will or can affect the air flow through the lower reach of the conveyor 17 so as to prevent satisfactory densification of the stratum b and/or c. The density D of the stratum a is always greater than that of the stratum b or c. The present invention renders it possible to specifically influence the density D of the stratum a, b and/or c so as to ensure that the actual density curve will more closely approximate the ideal density curve I.

The evaluation of densities which are ascertained by the monitoring device 43 at different distances from the lower reach of the conveyor 17 and the processing of the corresponding signals for the purpose of achieving optimal or more satisfactory densities in the strata a, b and c is effected by the control circuit 49a which directly influences the various servomotors, i.e., the parameters which determine the characteristics of the tobacco stream 58. The scanning circuit 50 transmits a series of impulses during each scanning of the diodes in the array of the detector forming part of the monitoring device 43. Such impulses denote the density of the stream 58 at different distances from the lower reach of the conveyor 17. The scanning frequency (e.g., approximately 300 kHz) is determined by a pulse generator 94 which is connected with the scanning circuit 50. If the diode array of the detector in the monitoring device 43 contains a total of 1024 diodes, the analog-digital converter 65' digitalizes a total of 1024 signals in the course of each scanning operation and such signals are transmitted to the corresponding inputs of the AND gates 88a–88c. The other input of each of the AND gates 88a–88c receives a signal from the associated counter 89a, 89b, 89c which is started at the begin of each density measuring operation. The setting of the first counter 89a is such that it transmits a signal to the right-hand input of the AND gate 88a during the transmission of first 400 pulses from the converter 65'. In other words, the AND gate 88a transmits to the memory 90a a total of 400 signals denoting the densities in various substrata of the stratum a of the tobacco stream 58. Thus, the first 400 signals are processed in the first circuit arrangement 87a of FIG. 9 while the other two circuit arrangements 87b and 87c are idle. This is due to the fact that, during such stage of the operation, the right-hand inputs of the AND gates 88b and 88c do not receive signals from the respective counters 89b, 89c. The signals which are transmitted by the AND gate 88a are stored in the memory 90a which is addressed by the comparator 91a to individually compare each freshly received signal with the corresponding signal in the reference memory 92a. The signals which are stored in the memory 92a denote the desired or ideal densities of the corresponding substrata of the stratum a of the tobacco stream 58 at the corresponding distances H (in mm) from the lower reach of the conveyor 17. The comparator 91a transmits a signal to the amplifier 93a and servomotor Xa when the signal which is received from the memory 90a deviates from the corresponding signal in the memory 92a. The servomotor or servomotors Xa then vary one or more parameters which influence the density of the stream 58 in a manner to ensure that the density D of the stratum a comes nearer to the ideal density of the stream, e.g., to ensure that the density of stratum a will at least correspond to that which is denoted by the corresponding portion of the curve R in FIG. 8. The arrangement may be such that the comparator 91a transmits a signal only when the monitored density of a particular substratum of the stratum a deviates from the optimum density (as denoted by the corresponding bit of information in the reference memory 92a) by more than a preselected minimum value.

It is advisable and important to ensure that the density of the stratum a will not exceed the density which is denoted by the corresponding portion of the curve R, e.g., that such density does not rise to the value which is designated by the corresponding portion of the (less satisfactory) density curve S of FIG. 8. Moreover, the circuit arrangement 87a can be designed to transmit signals to a single servomotor (e.g., 52a) if the monitored density of the stratum a deviates rather slightly from the desired density and to transmit signals to two or more servomotors (e.g., to the servomotors 52a, 84a and/or 85a) when the deviation of monitored density of the stratum a from the desired density is more pronounced. One way of reducing the density of the stratum a is to reduce the speed and/or the quantity of tobacco shreds which are conveyed through the channel A' of the duct 47 to form the uppermost stratum of the tobacco stream 58 at the underside of the lower reach of the conveyor 17. The density in the stratum a can be reduced even more rapidly and effectively if the reduction of speed and/or quantity of tobacco shreds in the channel A' takes place simultaneously with a reduction of the rate of air flow through the slots between the louvers 46a.

If the density of the stratum a is too low, it can be increased by accelerating the conveyor portion 12a via servomotor 85a and by simultaneously (or only if necessary) changing the direction of air flow and/or the rate of air flow through the slots between the louvers 46a (servomotors 52a and 84a).

Upon completion of transmission of the first 400 signals from the output of the converter 65', the signal at the output of the counter 89a disappears and this counter is automatically reset to zero. This terminates the transmission of signals to the memory 90a in the first circuit arrangement 87a. When the converter 65' transmits the signal No. 401, the output of the second counter 89b transmits a signal which enables the AND gate 88b to transmit signals to the memory 90b of the second circuit arrangement 87b. The stratum b is assumed to have a thickness of approximately 4 mm, i.e., it is disposed at a distance of between 4 and 8 mm from the lower reach of the conveyor 17. The circuit arrangement 87b then processes the signals Nos. 401 to 800 whereupon the counter 89b ceases to transmit a signal to the right-hand input of the gate 88b so that the transmission of signals to the memory 90b is terminated. While the memory 90b receives signals from the AND gate 88b, the comparator 91b compares such signals with the corresponding reference signals of the memory 92b and causes the amplifier 93b to actuate the servomotor or servomotors Xb when a correction of density D in the median stratum b of the tobacco stream 58 is desirable or necessary. The signals which appear at the output of the amplifier 93b can actuate the servomotor 52b, 84b and/or 85b. When the circuit arrangement 87b is deactivated, the input Z of the counter 89c receives a signal from the scanning circuit 50 and transmits a signal to the right-hand input of the AND gate 88c which begins to transmit signals from the converter 65' to the memory 90c for comparison with the corresponding signals in the memory 92c. If the difference between the pairs of compared signals is sufficiently pronounced, the amplifier 93c transmits a signal to the servomotor(s) Xc, e.g., to the servomotor 52c, 84c and/or 85c of FIG. 6. The thickness of the stratum c of the tobacco stream 58 is assumed to equal or approximate 4 mm, i.e., the overall height of the tobacco stream 58 is assumed to be in the range of 12 mm and the stratum c is assumed to be at a distance of approximately 8 mm from the reference plane which is the plane of the underside of the lower reach of the conveyor 17. The distribution of diodes in the detector of the monitoring device 43 may but need not necessarily be uniform. For example, the number of diodes for measurement of density in the stratum c can be less (e.g., approximately half) the number of diodes which receive signals denoting the density of the stratum a or b.

It will be noted that the apparatus of FIGS. 6 and 9 allows for the building of a tobacco stream which consists of several layers or strata (each of which can contain or consist of one and the same type of tobacco shreds or at least one of which can contain shreds which are different from those in the other stratum or strata) as well as for influencing of the make-up of each individual stratum in such a way that the density of the respective stratum closely approximates or even matches the optimum value. It is further clear that the rate of tobacco delivery via channel A' need not match the rate of tobacco delivery via channel B' and/or C', i.e., that the stream 58 can built of several strata each of which contains a different quantity of tobacco shreds. Thus, the apparatus of FIGS. 6 and 9 permits for a stream formation in accordance with a preselected pattern as regards the thickness and/or density and/or other characteristics of two or more strata.

In accordance with a presently preferred embodiment of the invention, the apparatus of FIGS. 6 and 9 can be used for the making of a so-called composite tobacco filler wherein a core consisting of or containing a first fibrous material is surrounded by a tubular envelope or shell consisting of or containing a different second fibrous material. Composite fillers of such type are described in the commonly owned copending patent application Ser. No. 557,735 filed Dec. 2, 1983 by Günter Wahle et al. Thus, the channels A' and C' of FIG. 6 can supply tobacco shreds of the type used to form the tubular envelope and the channel B' can be used to supply shreds of the type used to form the core. The formation of such a composite filler or stream can be accurately monitored and regulated by the apparatus of FIGS. 6 and 9 so as to ensure that the quantity of tobacco in the core will match the optimum quantity, that the core will be located centrally of the tubular envelope, that the density of the core and of the envelope will be acceptable and/or that the orientation of shreds in the core and/or envelope is also acceptable.

Figure 7:
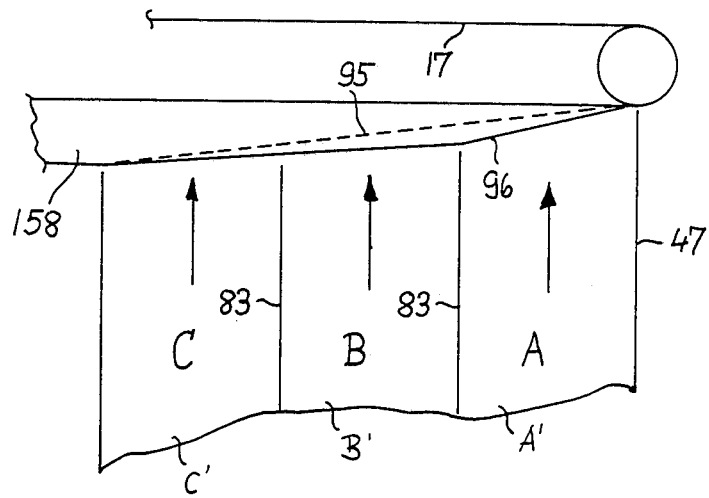
FIG. 7 illustrates a portion of a further stream building unit.

Referring to FIG. 7, the improved apparatus also permits for the making of a tobacco stream 158 which, as already mentioned above, contains two or three different strata or layers. This can be achieved by the simple expedient of regulating the rate of admission of tobacco shreds via channels or passages A', B' and C' to ensure the formation of satisfactory strata in the portions A, B and C of the channel 16 of the stream building unit. In accordance with the presently prevailing technique, a tobacco stream is built in such a way that its height or thickness (as considered at right angles to the plane of the respective reach of the tobacco conveyor 17) increases gradually, i.e., that the growing tobacco stream resembles a wedge as indicated in FIG. 7 by the broken line 95. The apparatus of the present invention renders it possible to regulate the rate of tobacco delivery via passage or channel A' independently of the rate of tobacco delivery via passage or channel B' and/or C' so that the growing tobacco stream can assume a shape as indicated in FIG. 7 by the solid line 96. This is but one of the various modes of building the tobacco stream with resort to a mechanism which can supply tobacco shreds in a plurality of discrete passages. If the rate of tobacco delivery via passage or channel A' is increased so as to build a stream whose outline is indicated by the line 96, the rate of tobacco delivery via passage or channel B' and/or C' is reduced accordingly so as to ensure that the quantity of tobacco shreds per unit length of the fully grown stream 158 approximates or matches the desired quantity (normally sufficiently in excess of the required quantity in the cigarette rod 28 to ensure that the height of each and every increment of the trimmed or equalized stream will match the distance between the cutter or cutters of the trimming device 19 and the lower reach of the conveyor 17). The formation of a relatively thick first stratum (of tobacco shreds which are supplied via passage or channel A') is often desirable and advantageous because this increases the likelihood that the density of the major portion of the resulting stream 158 will match or closely approximate the desired or optimum value. This will be readily appreciated since the condensation of tobacco shreds in the stratum nearest to the conveyor 17 is more pronounced than in the neighboring layers due to the fact that the material of the first stratum is subjected to the compacting action of the suction chamber 18 for a longer interval of time.

Referring again to FIG. 8, it will be seen that the control circuit 49a can also influence the servomotor 51 for the valve 44a in the conduit 44b between the outlet of the suction chamber 18 and the intake of the suction generating device (not shown in FIG. 6). This feature is also incorporated in the apparatus which embodies the structure of FIG. 7 to thus further enhance the adjustability of density of the first stratum of the tobacco stream 158, i.e., of the stratum which is immediately adjacent to the lower reach of the conveyor 17, by influencing the subatmospheric pressure in the chamber 18. As a rule, or at least in many instances, the servomotor 51 can be actuated in response to signals which denote the density of the stratum a of the tobacco stream.

The apparatus of FIGS. 6 and 9 and the apparatus of FIG. 7 render it possible to assemble the tobacco stream 58 or 158 of modules (strata) which can be influenced in a number of ways so that they together constitute a superior stream and thereafter a superior filler of a continuous cigarette rod. These apparatus (as well as the apparatus of FIGS. 2 to 5) can influence the formation of the stream 58 or 158 in the earliest stages of formation, i.e., even while the particles of fibrous material are on their way into the stream building zone (channel 16) proper, and the influencing of any stratum can be carried out independently of the influencing of the other stratum or strata. Each stratum can be influenced with a view to ensure that the corresponding part of the stream exhibits optimum characteristics regarding density, the percentage of recirculated surplus tobacco and the orientation of fibers therein as well as that the stream 58 or 158 in its entirety exhibits optimum characteristics which enhance the appearance, weight, resistance to deformation, density of the ends and/or other features of the finished products. Such differentiated influencing of various strata of the stream is not possible in accordance with heretofore known proposals in spite of the conventionality of testing of various substances with X-rays. As mentioned above, the first stratum a of the stream 158 can contain more material than the other stratum or strata (e.g., the stratum which is nearest to the lower reach of the conveyor 17 can contain more fibrous material than the other strata combined). Such non-linear formation of the stream 158 is often desirable on the ground that the consolidation of the first stratum is much more predictable than that of the other stratum or strata. This is due to the fact that the consolidation of the first stratum begins during the actual formation of such stratum and continues during the formation of the next-following stratum or strata. This results in the formation of a stream whose homogeneousness is surprisingly high and much more satisfactory than that of streams which are formed in accordance with heretofore known proposals.

The apparatus of FIGS. 6 and 9 and/or the apparatus of FIG. 7 can also regulate the percentage of discard or short tobacco (i.e., of recycled surplus tobacco) in the stream 58 or 158. Such regulation is often desirable and advantageous because it reduces the likelihood of density variations, not only as considered transversely of the direction of travel of the stream (i.e., at right angles to the reference plane which is defined by the lower reach of the conveyor 17) but also as considered in the longitudinal direction of the stream. The normally shorter shreds of surplus tobacco are free to penetrate into the interstices between the longer (untrimmed) shreds and thus contribute to greater density of the stream.

Each embodiment of the improved apparatus exhibits the advantage that its inertia is practically nil, i.e., that it can effect one or more necessary adjustments practically without any delay so that the number of rejects is negligible. At the present time, the apparatus of the present invention can be used with particular advantage to build a composite stream or filler wherein a core of first material (e.g., discard tobacco) is surrounded by a tubular envelope or shell of a different second material (e.g., long shreds of tobacco leaf laminae). This will be readily appreciated since the formation of such composite streams or fillers necessitates or renders desirable practically instantaneous corrective measures when the core is not at the center of the stream or filler, when the quantity of material forming the core is excessive or too low and/or when the density of the tubular envelope is unsatisfactory. All in all, the method and apparatus of the present invention allow for a regulation of the formation of a tobacco stream with a degree of precision which cannot be achieved in heretofore known apparatus. Moreover, the adjustment can be carried out with less delay (i.e., the inertia of the apparatus is lower) than in heretofore known apparatus.

It will be noted that the improved method and apparatus, which render it possible to ascertain the densities of various strata and substrata of the tobacco stream 58 or 158 at different distances from the reference plane, facilitate a much more predictable formation of a satisfactory tobacco stream and render it possible to greatly reduce the number of rejects. Thus, the improved method and apparatus render it possible to influence the formation of the stream within a wide range and to a different extent in each and every stratum of the stream. This leads to the formation of a tobacco stream which is much more homogenous than the tobacco streams which are formed in conventional apparatus, and the improved tobacco stream can be converted into the fillers of rod-shaped smokers' articles whose characteristics are more predictable and more uniform than the characteristics of presently produced articles.

As already mentioned above, the density of the stratum (such as the stratum a in the graph of FIG. 8) which is nearest to the conveyor 17 exerts a very pronounced influence upon the quality of the tobacco stream and of the articles which embody portions of such stream. The density of the stratum a depends considerably upon the selected pressure in the suction chamber 18. Such pressure can greatly influence the formation of the tobacco stream and the density of the stratum a nearest to the conveyor 17 irrespective of whether the stream building zone is undivided (as shown in FIG. 2) or the tobacco channel 16 comprises a series of successive parts (such as the parts A, B, C shown in FIGS. 6 and 7). With reference to FIG. 3, the comparator 68 of the control circuit 48 can influence the servomotor 51 for the valve 44a in such a way that suction in the chamber 18 is ideally suited for the formation of a stratum -a that exerts a beneficial influence upon the densities of the other strata. Of course, the servomotor 51 is but one of the adjusting means which can influence the density of the stratum a because such density can be influenced by one or more additional servomotors including the servomotor 52 of FIG. 2 which can regulate the direction and/or the rate of air flow through the slots 46. Moreover, signals from the comparator 68 of the control circuit 49 can be used to regulate another adjusting means which even more directly influences the rate of tobacco delivery into the channel 16 to thus further facilitate a highly accurate determination of density of the stratum a which is nearest to the conveyor 17 and exerts a very pronounced influence upon the density of the entire tobacco stream and of the fillers of finished rod-shaped articles.

As mentioned above, the density monitoring device 29 can also employ a source of X-rays and a suitable detector which forms a density image of various layers of the filler, i.e., of the trimmed and compacted tobacco stream 58 or 158. If such is the case, the evaluating circuit 54 of FIG. 2 can be identical with or clearly analogous to the evaluating circuit 48 which latter receives signals from the detector of the density monitoring device 43. If the monitoring device 29 also employs a source of X-rays, and if the detector of such monitoring device corresponds to the diode or CCD-array 79 of FIG. 4, the row of diodes in such detector extends at right angles to the direction of lengthwise movement of the cigarette rod 28. The monitoring device 29 can serve the additional purpose of monitoring the density of the filler as considered in the axial direction of the cigarette rod 28. This renders it possible to ascertain those variations of density which take place in the longitudinal direction of the rod 28 and to thus determine the density of tobacco at the ends of the cigarettes 32. The output of the evaluating circuit 54 is then connected to an ejecting device (as mentioned above, such ejecting device is preferably installed in the filter tipping machine 37) which segregates unsatisfactory cigarettes (namely, those having tobacco fillers with end portions of unsatisfactory density) from the remaining cigarettes, either before or after the plain cigarettes are united with filter rod sections to form therewith filter cigarettes of unit length or multiple unit length. Still further, the output of the evaluating circuit 54 can transmit signals to the servomotor 53 which influences the level of the cutter or cutters of the trimming device 19 and hence the quantity of tobacco in the equalized tobacco stream 58, i.e., in the filler of the cigarette rod 28.

As also mentioned above, the utilization of a two-dimensional diode or CCD-matrix (such as the matrix 79' of FIG. 5) in the detector of the density monitoring device 43 and/or 29 renders it possible to ascertain and regulate or adjust certain other characteristics of the tobacco stream 58 or 158. Scanning of several neighboring rows 81' of diodes in such a two-dimensional matrix can furnish information pertaining to the characteristics of the still image of density distribution of the stream (such image is obtained by exposing the rows 81' of diodes to the action of pulsating X-rays) which, in turn, facilitates a determination of the orientation of shreds in the tobacco stream and the generation of signals which can influence such orientation, e.g., for the purpose of varying the density of one or more strata of the tobacco stream. For example, the orientation of shreds in the tobacco stream can be influenced by changing the direction of air flow through the slots 46 of the duct 47 shown in FIG. 2. Scanning of a twodimensional matrix of diodes takes place substantially in the same way as the scanning of the unidimensional array of diodes forming the row 81 of FIG. 4 except that the rows 81' are scanned one after the other so that the interval of scanning is longer than in the case of a unidimensional array. However, the utilization of a twodimensional matrix allows for determination of other characteristics which can be influenced in the aforedescribed manner to further improve the quality of the tobacco stream and of the products containing portions of such stream.

For the sake of simplicity, the preceding description of scanning of the unidimensional or two-dimensional density image was described as involving the generation of a discrete signal for each and every diode. In actual practice, it normally is preferred to average the intensities of a selected selected number of successive signals of each diode, and to utilize such averaged signals for variation of one or more parameters which influence the characteristics of the tobacco stream. This prevents undesirable abrupt and pronounced changes during the formation of the stream. The manner in which the values of several successively detected signals of each diode can be averaged for further processing is notoriously old and need not be described here.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A method of forming and processing a stream of fibrous material, particularly a stream of tobacco particles for the making of cigarettes and analogous smokers' products, comprising the steps of building a continuous stream including delivering fibrous material into an elongated path to thus form successive increments of the stream and moving such increments along the path, said building step being a function of a plurality of different parameters including the rate of delivery of fibrous material into the path, the dimensions of fibrous material and the orientation of fibrous material in the path; monitoring the density of the moving stream at a plurality of different distances from a reference plane which is at least substantially parallel to the path; generating signals which denote the monitored density at such different distances from the reference plane; and varying at least one of said parameters as a function of variations of at least one of said signals.

2. The method of claim 1, wherein said moving step includes utilizing a moving conveyor to define said path and said delivering step comprises supplying fibrous material to the conveyor.

3. The method of claim 2, wherein said supplying step includes conveying fibrous material in at least one current of air and directing the current of air against the conveyor, said moving step comprising attracting fibrous material to the moving conveyor by suction.

4. The method of claim 3, wherein the reference plane is defined by the moving conveyor and said one parameter determines the distribution of density in the stream, said varying step including varying said one parameter so as to establish a predetermined distribution of densities in the stream.

5. The method of claim 1, wherein said delivering step includes accumulating the stream in the form of several longitudinally extending sections whose characteristics can be influenced independently of each other, said monitoring step including separately ascertaining the density of each such section of the stream and said varying step including independently varying the parameters which determine the densities of the respective sections in dependency on variations of signals denoting the densities in the corresponding sections so that the distribution of densities in the sections of the stream matches a predetermined pattern of densities, as considered at right angles to the reference plane.

6. The method of claim 5, wherein said accumulating step includes building the respective sections in at least two successive stages.

7. The method of claim 6, wherein said accumulating step includes supplying to the path a first fibrous material during the first of said stages and a different second fibrous material during the second of said stages, said varying step including varying said one parameter so that the composition of the stream matches a predetermined pattern.

8. The method of claim 7, wherein said varying step further comprises varying at least one of said parameters so that the distribution of densities in the stream matches a predetermined pattern.

9. The method of claim 7, wherein said supplying step includes feeding a first fibrous material at a rate exceeding the rate at which the second fibrous material is supplied, the second fibrous material being supplied on top of the stream section which consists of said first fibrous material.

10. The method of claim 1, wherein said moving step includes utilizing a moving conveyor to define said path and said delivering step includes supplying fibrous material to the conveyor in a current of air, said moving step further including attracting the stream to the conveyor by suction and the reference plane being defined by the conveyor so that said monitoring step comprises ascertaining the density of the stream at a plurality of different distances from the conveyor including a range of distances nearest to the conveyor, said varying step including varying as a function of variations of density within said range of distances at least one parameter which influences the density of a stratum of the stream nearest to the conveyor so that the distribution of density in such stratum of the stream matches a predetermined pattern.

11. The method of claim 1, wherein said delivering step includes supplying into the path fibrous material containing shreds of different lengths, said varying step including increasing the percentage of shorter shreds in the course of said supplying step when the monitored density of the stream decreases.

12. The method of claim 1, wherein said monitoring step includes directing X-rays transversely across the stream so that at least some X-rays penetrate through the stream and the X-rays issuing from the stream in their entirety constitute an image denoting the distribution of density at said different distances from the reference plane, said varying step including varying a parameter which determines the distribution of density in the stream so tat the distribution matches a predetermined pattern.

13. The method of claim 12, wherein said signal generating step includes unidimensional linear scanning of the image.

14. The method of claim 12, wherein said monitoring step further includes pulsating the X-rays.

15. The method of claim 14, wherein said image is a two-dimensional still image.

16. The method of claim 15, wherein the fibrous material contains shreds and said image is further indicative of the orientation of shreds in the stream, said signal generating step including two-dimensional scanning of the image and said varying step including varying a parameter which influences the stream building step as a function of the detected orientation of shreds in the stream.

17. The method of claim 1, wherein said delivering and moving steps include utilizing currents of air to supply fibrous material to and to retain the thus supplied fibrous material in said path, said varying step including varying the quantity and/or the direction of air in such currents.

18. The method of claim 1, wherein said delivering step includes supplying fibrous material at a variable rate and said varying step includes varying the rate at which the fibrous material is supplied into said path.

19. The method of claim 1, wherein said delivering step comprises supplying fibrous material at a variable speed and said varying step includes varying the speed of fibrous material in the course of said supplying step.

20. The method of claim 1, wherein said delivering step comprises supplying into said path fibrous material in the form of shorter and longer shreds and said one parameter is the ratio of shorter shreds to longer shreds in the stream.

21. A method of forming and processing a stream of fibrous material, particularly a stream of tobacco particles for the making of cigarettes and analogous smokers' products, comprising the steps of building a continuous stream as a function of a plurality of different parameters; monitoring the density of the stream at a plurality of different distances from a reference plane which is at least substantially parallel to the stream, including directing X-rays transversely of the stream so that at least some of the X-rays penetrate through the stream and the X-rays issuing from the stream constitute or form part of an image denoting the distribution of density at said different distances from the reference plane; generating signals denoting the monitored density at such different distances from the reference plane; and varying at least one of said parameters as a function of variations of at least one of said signals.

22. The method of claim 20, wherein said signal generating step includes scanning said image.

23. The method of claim 20, wherein said varying step includes varying at least one parameter which influences the density of the stream so that the distribution of density in the stream at least approximates a predetermined pattern.

24. Apparatus for forming and processing a stream of fibrous material, particularly a stream of tobacco particles for the making of cigarettes and analogous smokers' products, comprising adjustable stream building means including a conveyor defining an elongated path and means for supplying to the conveyor fibrous material which accumulates and forms a continuous stream thereon; means for monitoring the density of the stream at a plurality of different locations, as considered transversely of said path, including means for generating signals denoting the monitored density at said plurality of locations; and means for adjusting said stream building means in response to deviation of at least one of said signals from a preselected value.

25. The apparatus of claim 24, wherein said signal generating means comprises a position sensitive detector.

26. The apparatus of claim 25, further comprising signal evaluating means interposed between said detector and said adjusting means.

27. The apparatus of claim 26, wherein said stream building means comprises a plurality of components each of which is arranged to form on said conveyor a separate stratum of the stream and said strata include a first stratum directly adjacent to said conveyor, said adjusting means including discrete adjusting elements for each of said components and said evaluating means including control means arranged to actuate each of said adjusting elements as a function of variations of signals denoting the densities of the respective strata.

28. The apparatus of claim 27, wherein each of said components comprises a discrete adjustable device for supplying fibrous material and said adjusting elements are arranged to adjust the respective supplying devices.

29. The apparatus of claim 28, wherein said evaluating means comprises a discrete actuating arrangement for each of said adjusting elements.

30. The apparatus of claim 26, wherein said monitoring means further comprises a source of X-rays and means for directing X-rays against the stream so that the radiation which penetrates through the stream impinges upon said position sensitive detector and forms thereon an image denoting the distribution of densities in the monitored portion of the stream.

31. The apparatus of claim 30, wherein said evaluating means includes means for scanning said image and control means for transmitting to said adjusting means second signals denoting the densities of various portions of the stream.

32. The apparatus of claim 31, wherein said detector comprises an array of diodes.

33. The apparatus of claim 31, wherein said detector comprises a CCD-array.

34. The apparatus of claim 31, wherein said detector is a unidimensional detector.

35. The apparatus of claim 31, wherein said detector is a two-dimensional detector.

36. The apparatus of claim 31, wherein said detector comprises an X-ray sensitive screen and a television camera for imaging X-rays onto said screen.

37. The apparatus of claim 31, wherein said detector comprises an X-ray amplifier.

38. The apparatus of claim 26, wherein said evaluating means comprises a control circuit having at least one output connected with said adjusting means.

39. The apparatus of claim 24, wherein said supplying means comprises means for delivering the fibrous material in at least one current of gaseous fluid and said adjusting means comprises means for regulating at least one characteristic of the gaseous fluid.

40. The apparatus of claim 39, wherein said characteristic is the speed of gaseous fluid.

41. The apparatus of claim 39, wherein said characteristic is the direction of flow of said gaseous fluid.

42. The apparatus of claim 39, wherein said characteristic is the quantity of gaseous fluid.

43. The apparatus of claim 24, wherein said supplying means comprises means for supplying at least two different types of fibrous material and said adjusting means includes means for regulating the quantity of one of said types of fibrous material in the stream.

44. The apparatus of claim 43, further comprising means for removing the surplus from the stream, said one type of fibrous material including such surplus.

45. The apparatus of claim 24, wherein said supplying means includes means for delivering fibrous material at a variable rate and said adjusting means includes means for varying the rate of delivery of fibrous material.

46. The apparatus of claim 24, wherein said supplying means includes means for delivering fibrous material at a variable speed and said adjusting means includes means for regulating the speed of fibrous material.

47. The apparatus of claim 24, wherein said supplying means includes means for delivering fibrous material in any one of a plurality of different directions and said adjusting means comprises means for selecting the direction of delivery of fibrous material.

48. A method of forming and processing a stream of fibrous material, particularly a stream of tobacco particles for the making of cigarettes and analogous smokers' products, comprising the steps of building a continuous stream including delivering fibrous material into an elongated path to thus form successive increments of the stream and moving such increments along the path; monitoring the density of the moving stream at a plurality of different distances from a reference plane which is at least substantially parallel to the path; and generating signals which denote the monitored density at such different distance from the reference plane.

49. A method of forming and processing a stream of fibrous material, particularly a stream of tobacco particles for the making of cigarettes and analogous smokers' products, comprising the steps of building a continuous stream; monitoring the density of the stream at a plurality of different distance from a reference plane which is at least substantially parallel to the stream, including directing X-rays transversely of the stream so that at least some of the X-rays penetrate through the stream and the X-rays issuing from the stream constitute or form part of an image denoting the distribution of density at said different distances from the reference plane; and generating signals denoting the monitored density at such different distance from the reference plane.

50. Apparatus for forming and processing a stream of fibrous material, particularly a stream of tobacco particles for the making of cigarettes and analogous smokers' products, comprising stream building means including a conveyor defining an elongated path and means for supplying to the conveyor fibrous material which forms a continuous stream thereon; and means for monitoring the density of the stream at a plurality of different locations, as considered transversely of said path, including means for generating signals denoting the monitored density at said plurality of locations.

* * * * *

UNITED STATES PATENT AND TRADEMARK OFFICE
CERTIFICATE OF CORRECTION

PATENT NO. : 4,785,830                 Page 1 of 2
DATED : November 22, 1988
INVENTOR(S) : Henning MÖLLER et al.

It is certified that error appears in the above-identified patent and that said Letters Patent is hereby corrected as shown below:

```
On the title page [75]:  --Gerhard Ramsch,-- should be inserted,
after "Hartmann," and "both" should read --all--.
Col.  3, line 23, "f" should read --of--.
Col. 15, line 39, "e access" should read --excess--.
Col. 16, line 21, "signal" should read --signals--;
         line 30, "m" should be italicized;
         line 31, "n" should be italicized;
         line 32, "m" should be italicized.
Col. 18, line 21, --Z-- should be inserted after "inputs";
         line 64, "a" should be italicized;
         line 67, "a" should be italicized.
Col. 19, line  1, "c" should be italicized;
         line  5, "a" (first occurrence) and "b" should
be italicized;
         line  6, "a" (first occurrence) should be
italicized;
         line  7, "c" should be italicized;
         line  8, "a" and "b" should be italicized;
         line  9, "c" should be italicized;
         line 11, "a" (second occurrence) should be
italicized;
         line 14, "b" and "c" should be italicized;
         line 15, "a" and "b" should be italicized;
         line 16, "c" should be italicized;
         line 17, "a" and "b" should be italicized;
         line 18, "c" should be italicized;
         line 24, "a" and "b" should be italicized;
         line 25, "c" should be italicized.
```

UNITED STATES PATENT AND TRADEMARK OFFICE
CERTIFICATE OF CORRECTION

PATENT NO. : 4,785,830

DATED : November 22, 1988

INVENTOR(S) : Henning MÖLLER et al.

It is certified that error appears in the above-identified patent and that said Letters Patent is hereby corrected as shown below:

Col. 25, line 49, "selected" (second occurrence) should be deleted.
Col. 30, line 41, "loca-" should be deleted.
    line 42, "tions, as considered transversely" should be deleted, and --distances from a reference plane which is at least substantially parallel to-- should be inserted before "of";
    line 43, --a plurality of-- should be inserted after "generating", and --each-- should be inserted after "signals";
    line 44, --one of-- should be inserted after "at", and --distances from said reference plane-- should be inserted after "of".

Signed and Sealed this

Twentieth Day of November, 1990

Attest:

HARRY F. MANBECK, JR.

*Attesting Officer*      *Commissioner of Patents and Trademarks*